(12) United States Patent
John et al.

(10) Patent No.: US 8,353,837 B2
(45) Date of Patent: Jan. 15, 2013

(54) MODULATION AND ANALYSIS OF CEREBRAL PERFUSION IN EPILEPSY AND OTHER NEUROLOGICAL DISORDERS

(75) Inventors: Michael Sasha John, Larchmont, NY (US); Benjamin D. Pless, Atherton, CA (US); Brett Wingeier, San Francisco, CA (US)

(73) Assignee: NeuroPace, Inc., Mountain View, CA (US)

( * ) Notice: Subject to any disclaimer, the term of this patent is extended or adjusted under 35 U.S.C. 154(b) by 389 days.

(21) Appl. No.: 12/700,692

(22) Filed: Feb. 4, 2010

(65) Prior Publication Data

US 2010/0137937 A1 Jun. 3, 2010

Related U.S. Application Data

(60) Division of application No. 11/404,579, filed on Apr. 14, 2006, now Pat. No. 7,819,812, which is a continuation-in-part of application No. 11/014,628, filed on Dec. 5, 2004, now Pat. No. 7,341,562.

(51) Int. Cl.
   *A61B 8/06* (2006.01)

(52) U.S. Cl. ............. 600/454; 607/62; 607/45; 600/378

(58) Field of Classification Search .................. 600/378, 600/454; 607/45, 62
   See application file for complete search history.

(56) References Cited

U.S. PATENT DOCUMENTS

| | | | |
|---|---|---|---|
| 4,817,627 A | 4/1989 | Cohen et al. | |
| 4,893,630 A | 1/1990 | Bray, Jr. | |
| 5,845,639 A * | 12/1998 | Hochman et al. | 600/407 |
| 6,006,124 A | 12/1999 | Fischell et al. | |
| 6,016,449 A | 1/2000 | Fischell et al. | |
| 6,018,682 A | 1/2000 | Rise | |
| 6,468,219 B1 * | 10/2002 | Njemanze | 600/454 |
| 6,629,990 B2 | 10/2003 | Putz et al. | |
| 6,792,302 B2 | 9/2004 | Wintermark et al. | |
| 6,810,285 B2 | 10/2004 | Pless et al. | |
| 2002/0161292 A1 | 10/2002 | Wintermark et al. | |
| 2002/0169485 A1 * | 11/2002 | Pless et al. | 607/48 |
| 2003/0074032 A1 | 4/2003 | Gilner | |
| 2003/0176892 A1 | 9/2003 | Shalev | |
| 2004/0039270 A1 | 2/2004 | Keller et al. | |
| 2004/0082978 A1 | 4/2004 | Harrison et al. | |
| 2004/0092809 A1 * | 5/2004 | DeCharms | 600/410 |
| 2005/0283200 A1 | 12/2005 | Rezai et al. | |

OTHER PUBLICATIONS

U.S. Appl. No. 11/925,655 Office Action mailed Jun. 28, 2010.
Gotman, J., Automatic Seizure Detection: Improvements and Evaluation, Electroencephalogr. Clin. Neurophysiol. (1990) 76(4): 317-24.
Wagner, H. R., et al., Suppression of Cortical Epileptiform Activity by Generalized and Localized ECoG Desynchronization, Electroencephalogr. Clin. Neurophysiol. (1975) 39(5): 499-506.
Tavalin, S.J., et al., Mechanical Perturbation of Cultured Cortical Neurons Reveals a Stretch-Induced Delayed Depolarization, J. Neurophysiol. (1995) 74(6): 2767-2773.

(Continued)

*Primary Examiner* — Carl H Layno
*Assistant Examiner* — Natasha Patel

(57) ABSTRACT

A system including an implantable neurostimulator device capable of modulating cerebral blood flow to treat epilepsy and other neurological disorders. In one embodiment, the system is capable of modulating cerebral blood flow (also referred to as cerebral perfusion) in response to measurements and other observed conditions. Perfusion may be increased or decreased by systems and methods according to the invention as clinically required.

3 Claims, 16 Drawing Sheets

OTHER PUBLICATIONS

Bahar, S. et al., The Relationship Between Cerebral Blood Volume And Oxygenation Following BiPolar Stimulation of the Human Cortex: Evidence for an Initial Dip, Epilepsia 2004; 45 Suppl 7, 107-108.
Matsuura, T, et. al., Hemodynamics Evoked by Microelectrical Direct Stimulation in Rat somatosensory Cortex, Comp. Biochem. Physiol. A. Mo. 1 Integr. Physiol. Sep. 1999; 124(1): 47-52.
U.S. Appl. No. 11/925,668, filed May 26, 2010.
U.S. Appl. No. 11/925,668 Amendment filed May 26, 2010.
Tarver, T. et al., "An Implantable Neurocybernetic Prosthesis System," http://www.ncbi.nlm.nlh.gov, Jun. 12, 2007.
Activa Therapy Overview, http://www.medtronic.com/physician/activa/index.html, Jun. 5, 2007.
U.S. Appl. No. 11/925,668, Office action mailed Mar. 1, 2010.
Office Action (Final Rejection) mailed Aug. 19, 2010 for U.S. Appl. No. 11/925,668.
Amendment Filed on Dec. 20, 2010 for U.S. Appl. No. 11/925,668.
Notice of Allowance mailed on Dec. 16, 2010 for U.S. Appl. No. 11/925,655.

* cited by examiner

MODULATION AND ANALYSIS OF CEREBRAL PERFUSION IN EPILEPSY AND OTHER NEUROLOGICAL DISORDERS

CLAIM OF PRIORITY AND RELATED APPLICATIONS

This is a divisional of application Ser. No. 11/404,579, now U.S. Pat. No. 7,819,812 filed Apr. 14, 2006, which is a continuation-in-part of application Ser. No. 11/014,628, filed Dec. 15, 2004, now U.S. Pat. No. 7,341,562, each of which applications are incorporated by reference herein in the entirety.

BACKGROUND

1. Technical Field

The invention relates generally to medical devices for treating neurological disorders such as epilepsy, and more particularly to a system incorporating an implantable device capable of measuring and modulating cerebral blood flow.

2. Background

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20-30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices do not perform any detection of neural activity and apply electrical stimulation to neural tissue surrounding or near implanted electrodes somewhat indiscriminately; they are not responsive to relevant neurological conditions. Responsive stimulation, in which neurological activity is detected and electrical stimulation treatment is applied selectively, is in clinical trials at the time of this writing.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide substantial clinical benefit.

The Activa device from Medtronic is a pectorally implanted continuous deep brain stimulator intended primarily to treat Parkinson's disease. In operation, it continuously supplies an intermittent electrical pulse stream to a selected deep brain structure where an electrode has been implanted. Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation above a certain level may cause significant neurological deficit with clinical symptoms including loss of speech, sensory disorders, or involuntary motion. Accordingly, and to improve therapeutic efficacy over indiscriminate continuous stimulation, research has been directed toward automatic responsive epilepsy treatment based on a detection of imminent seizure.

A typical epilepsy patient experiences episodic attacks or seizures. Those events, neurological states, and epileptiform activity evident on the EEG shall be referred to herein as "ictal."

Most prior work on the detection and responsive treatment of seizures via electrical stimulation has focused on analysis of electroencephalogram (EEG) and electrocorticogram (ECoG) waveforms. In common usage, the term "EEG" is used to refer to signals representing aggregate neuronal activity potentials detectable via electrodes applied to a patient's scalp, though the term can also refer to signals obtained from deep in the patient's brain via depth electrodes and the like. Specifically, "ECoGs" refer to signals obtained from internal electrodes near the cortex of the brain (generally on our under the dura mater), but is often used to refer to direct brain signals from deeper structures as well; an ECoG is a particular type of EEG. Unless the context clearly and expressly indicates otherwise, the term "EEG" shall be used generically herein to refer to both EEG and ECoG signals, regardless of where in the patient's brain the electrodes are located.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified, and may be used to facilitate intervention before clear electrographic onset or clinical onsets occur. This capability would be considered seizure anticipation, in contrast to the detection of a seizure or its onset. Seizure anticipation is much like weather prediction—there is an indication the likelihood has increased that a seizure will occur, but when exactly it will occur, or even if it will occur is not certain.

U.S. Pat. No. 6,018,682 to Rise for "Implantable Seizure Warning System," issued Jan. 25, 2000, describes an implantable seizure warning system that implements a form of the Gotman system. See, e.g., J. Gotman, *Automatic Seizure Detection: Improvements and Evaluation*, Electroencephalogr. Clin. Neurophysiol. 1990; 7(4): 317-24. However, the system described therein uses only a single detection modality, namely a count of sharp spike and wave patterns within a limited time period, and is intended to provide a warning of impending seizure activity in spite of a lack of evidence that spike and wave activity is sufficiently anticipatory of seizures. This is accomplished with relatively complex processing, including averaging over time and quantifying sharpness by way of a second derivative of the signal. The Rise patent does not disclose how the signals are processed at a low level, nor does it explain detection criteria in any specific level of detail.

U.S. Pat. No. 6,016,449 to Fischell, et al., for "System for Treatment of Neurological Disorders," issued Jan. 18, 2000 (which is incorporated by reference as though set forth in full herein), describes an implantable seizure detection and treatment system. In the Fischell system, various detection methods are possible, all of which essentially rely upon the analysis (in either the time domain or the frequency domain) of processed EEG signals. Fischell's controller is preferably implanted intracranially, but other approaches are also possible, including the use of an external controller. The processing and detection techniques applied in Fischell are generally well suited for implantable use. When a seizure is detected, the Fischell system applies responsive electrical stimulation to terminate the seizure, a capability that will be discussed in further detail below.

All of these approaches provide useful information, and in some cases may provide sufficient information for accurate detection, and/or anticipation of most imminent epileptic seizures.

It has been found that many clinical neurological disorders are associated with abnormal blood flow patterns in the brain. These include epilepsy, migraine, aging, movement disorders, and psychiatric disorders. One result of abnormal blood flow is an imbalance between cerebral oxygen supply and demand, although other aspects, such as removal of metabolic waste products, also contribute to generation of the disorders. This is thought to play an important role in the development of cerebral injury as well as generation of neurological events common to various disorders. It would therefore be advantageous to employ a system or method to monitor such abnormal blood flow patterns, either in isolation or in connection with abnormal electrographic activity, to identify the status of the disease state and to monitor the short-term and/or long-term progression of the disease state with the intention of correcting the abnormal or insufficient blood flow patterns to provide clinical benefit. Such monitoring is preferably accomplished within the therapy delivery device (often a neurostimulator) to automatically adjust therapy delivery to the patient to more optimally bring about beneficial changes in brain blood flow patterns either acutely or more long term. Therapy delivery may be direct brain electrical stimulation, spinal cord stimulation, brain stem or peripheral nerve stimulation, or may be magnetic stimulation, somatosensory stimulation, or drug delivery. However, monitoring may include means not included in the therapy delivery device, with therapy being adjusted by a clinician. Monitoring of the brain blood flow can be accomplished by the periodic use of non-invasive imaging techniques including SPECT, PET, SISCOM, infrared, ultrasound, or impedance techniques.

As is well known, it has been suggested that it is possible to treat and terminate seizures by applying electrical stimulation to the brain. See, e.g., U.S. Pat. No. 6,016,449 to Fischell et al., and H. R. Wagner, et al., *Suppression of Cortical Epileptiform Activity by Generalized and Localized ECoG Desynchronization*, Electroencephalogr. Clin. Neurophysiol. 1975; 39(5): 499-506. It has further been found that electrical stimulation can modulate blood flow in the brain. It has been found that cortical stimulation increases blood flow within hundreds of milliseconds at the site of stimulation (T. Matsuura et al., *Hemodynamics Evoked By Microelectrical Direct Stimulation In Rat somatosensory Cortex*, Comp. Biochem. Physiol. A. Mo. 1 Integr. Physiol. (1999) September; 124(1): 47-52; see also S. Bahar et al., *The Relationship Between Cerebral Blood Volume and Oxygenation Following BiPolar Stimulation of the Human Cortex: Evidence for an Initial Dip*, AES December 2004 New Orleans Poster Session). Stimulation of other brain structures or through the use of transcranial magnetic stimulation can produce patterns of blood flow changes (including increases or reductions of blood flow) in targeted areas.

At the current time, there is no known implantable device that is capable of treating abnormal neurological conditions, including seizures, by changing cerebral perfusion either acutely or chronically. Furthermore, there is no known implantable device that is capable of detecting and/or anticipating seizures or other neurological events based on cerebral perfusion conditions and changes therein, alone or in combination with other observed conditions. As anticipated herein, modulation of blood perfusion in the brain may be employed for acute or chronic treatment of neurological conditions.

SUMMARY

A system according to the invention includes an apparatus, preferably implantable, capable of modulating cerebral blood flow and/or sensing changes in cerebral blood flow, either globally or locally, and responding thereto to achieve acute and/or chronic changes in cerebral blood flow.

The invention provides for the use of electrical stimulation and other modalities of stimulation (including transcranial magnetic stimulation) directed at a variety of anatomical targets to produce changes in perfusion and cortical blood flow to treat neurological disorders, including but not limited to epilepsy. Stimulation may be applied "open loop" (on a scheduled basis), or "closed loop" as a result of information from sensors, particularly blood flow, electrographic, or movement sensors. Therapy may also be provided on command by a physician, the patient, or a caregiver. Systems according to the invention may be adapted for implantable use, or may be partially or completely external to the patient.

Evaluation of perfusion, and also the modulation of perfusion, refers not simply to the general passage of fluid through the blood vessels to supply neural tissue, but also to the adequacy of the blood supply relative to the needs of the brain or relative to the symptoms of a disorder for which stimulation serves as treatment. Methods such as optical spectroscopy provide measures not only related to activation, but the individual concentrations of both oxyhemoglobin ($HbO_2$) and deoxyhemoglobin (HbR) result from a combination of physiological factors such as regional blood volume, blood flow, oxygen consumption, and waste product removal. The accumulation of $HbO_2$ in the brain is also dependent on both arterial inflow and venous outflow of a region. Rather than simply a form of circulation or hemodynamic monitoring, permitted by measurement or inference of the general perfusion of a region of tissue (e.g., various types of flowmetry), perfusion, here, includes a consideration, in the context of blood supply, of tissue's sensitivity to brain activation and oxygen levels, or, even more specifically, relative changes in brain activation and oxygen levels. Perfusion, therefore, includes the supply and demand aspects of blood flow, volume, and constituents with respect to the disorder and its treatment. Cerebral perfusion should be understood to relate to any aspect of providing tissue with sufficient blood to function in a healthy fashion while also removing waste products of cellular activity. Cerebral perfusion status is determined by, and may refer to, any of the following: cerebral blood volume, cerebral blood flow, blood gas composition, indexes of blood gas composition such as $HbO_2/(HbO_2+Hb)$, or $Hb_T$ ($Hb_{total}$), arterial oxygen content, venous oxygen content (which can be determined, for example, by locating two sensors appropriately) or others as are known to those skilled in the art.

Conceptually tissues or brain regions which can serve as neural targets for providing therapy can be classified as "associated" or "non-associated." Associated tissue is relatively related to a symptom of the disorder. For example, associated tissue may be a region related to the focus of seizure origin, or a region with abnormal metabolic activity which is related to the disorder. Non-associated tissue may be a region which is relatively less modulated by the disorder, compared to associated tissue, such as an area which is distal to a seizure focus, or an area of normal or abnormal metabolic activity which is relatively unrelated to, or unaffected by, the disorder. While the likelihood of being non-associated tissue generally increases as distance from an associated region increases, due to the tract and networks of the brain, measures such as covariance rather than proximity, relate more to whether a region adjacent to an associated area are also defined as such.

Electrical stimulation may be applied directly to the cortex, or alternatively to deeper brain structures, or to the brain stem, spinal cord or to cranial or peripheral nerves. Electrical stimulation, when it is applied, may be pulsatile in nature or of an arbitrary waveform including sine waves. Different stimulation patterns, and the location of the stimulation, may be varied depending upon the brain state. For example, a hypo-perfused seizure onset focus in the interictal state may receive a stimulation pattern specifically designed to maximize blood flow. As the brain transitions into a pre-seizure state as determined by characteristic changes in blood flow, electrographic evidence, or even by the patient feeling symptoms and communicating the information to the therapy device, the stimulation pattern may be beneficially changed to enhance blood flow in neural pathways (for instance in those pathways emanating from the seizure focus), or to decrease excitability at the seizure focus for example by stimulation of the caudate.

One system according to the invention includes an implanted control module, controllable via external equipment, that is capable of applying therapeutic intervention to alter cerebral blood flow via electrical, thermal, chemical, electromagnetic, or other therapy modalities set forth herein and described in greater detail below. Preferably, such stimulation is not provided continuously, but intermittently, and means are provided to verify the need and/or effects of blood flow stimulation according to the invention. For example, an external programmer may be used to command the implanted device to deliver stimulation, after which measurements are taken (via imaging techniques or other methods described herein, including automatic measurements taken by the implanted device) to verify the effects or progress of the therapy. Depending on the effects observed, the implanted device is programmed by the external programmer with a preferred therapy regimen.

In an embodiment of the invention, automatic measurements are taken by the implanted device via impedance plethysmography techniques. These measurements are recorded and later transferred to the external programmer via wireless telemetry, and may be used by a clinician to tailor therapy to the specific patient being treated.

In an embodiment of the invention, automatic measurements are taken by the implanted device via impedance plethysmography techniques. These measurement are recorded and later transferred to the external programmer via wireless telemetry, and may be used by a clinician to tailor therapy to the specific patient being treated.

A specific embodiment of a system according to the invention performs regular perfusion measurements and applies therapy automatically in response thereto. This embodiment includes an implanted control module, implanted electrodes on a seizure focus and on the caudate nucleus, and an implanted pulse oximetry perfusion sensor in the vicinity of the seizure focus. In addition, a perfusion sensor (with electrodes) may be implanted on the contralateral lobe from the seizure focus. After implant, baseline perfusion and electrographic data may be collected for at least several days and for several seizures while the patient recovers from surgery. Commanded stimulation studies may be performed to assess the affect of different stimulation parameters at the seizure focus and at the caudate on perfusion behavior. Stimulation at the seizure focus will generally increase perfusion (the seizure focus is generally hypo-perfused in the interictal period) whereas stimulation of the brain stem structures or the caudate may decrease perfusion.

The implanted control module monitors perfusion at the epileptogenic focus, taking pulsed measurements periodically, for example, every 30 seconds to save power. If sudden changes in perfusion are detected, the sampling rate (or other aspects of the sensing procedure) may be increased for improved resolution. The control module runs a therapy algorithm to increase the perfusion level at the epileptogenic focus to a target range by applying stimulation as programmed within a preset range of allowed parameters (pulse amplitude, pulse width, number of pulses in a burst, pulse to pulse interval, interval between bursts, rate of change allowed from burst to burst). If the perfusion level in the area of the seizure focus increases above the target range, the algorithm calls for the control module to stimulate other brain structures such as the caudate or structures in the contralateral hemisphere in an attempt to bring the perfusion level down to a target range (this target range may be different than the target used when stimulating the focus directly). Alternatively, tissue near the focus, but which does not participate in the seizure, may be stimulated in order to decrease blood flow to the focus. Activating adjacent tissue that is perfused by a vascular branch that can compete with the branch supplying the seizure focus may be such an alternative target. The patient or a caregiver may be alerted if a trend towards increased perfusion of the epileptogenic focus occurs despite caudate stimulation. This would allow the use of an increased dose of antiseizure medication only when a breakthrough seizure is likely to occur.

Episodes of disorders such as migraine are progressive in that these will typically follow a sequence of events, for example, aura, uncomfortable pressure, headache, and allodynia. These can be representative of different biological events which also can occur sequentially, such as, hypothetically, spreading depression, activation/sensitization of the trigeminovascular system, vasodilation/neurogentic inflammation, and central modulation of migraine pain. The observation that disorders such as migraine are sequential, or at least have stages, is evident in differential response to triptan intervention, where its provision early during an attack provides much greater benefit, specifically when it is provided prior to the emergence of allodynia. Epileptic seizures are also generally sequential, but with a different sequence of steps. Accordingly, neurostimulation treatment during a disorder is advantageously modified according to what stage of the disorder is occurring and the time therapy is being applied. In one embodiment, sensed data, such as near-infrared spectroscopy (NIRS) data, is used to automatically provide an estimate of which step of a migraine sequence is occurring. The corresponding therapy parameters are then selected (for example, via a look-up table). Further, or as an alternative to using sensed data, when using an external patient programmer or other apparatus capable of transmitting information to the neurostimulator device, the patient can input information which can assist in determining which step in a sequence of steps is occurring. For example, if the patient indicates that allodynia is occurring, the neurostimulation treatment delivered before and after its manifestation can use different parameters and modalities, and further can be directed towards different structures in the brain. Additionally, the elapsed time from the beginning of an event, or from a symptom of the event (as indicated by sensed data or patient input) can also be used to provide stimulation parameters which are appropriate for the "predicted" step of the sequence.

It should be noted that epilepsy, migraine, and other neurological disorders treatable by a system according to the invention, vary greatly in symptomology and treatment strategies from patient to patient. To give one example, although perfusion has generally been observed to be pathologically low and increase just prior to an epileptic seizure, the reverse may be true in some patients or in some anatomical locations. Accordingly, the present invention as described in detail herein provides a framework for the diagnosis and treatment of neurological dysfunctions by sensing and responding to changes in cerebral blood flow, but specific treatment strategies could be determined, customized, and altered as clinical observations and experience dictate.

BRIEF DESCRIPTION OF THE DRAWINGS

These and other objects, features, and advantages of the invention will become apparent from the detailed description below and the accompanying drawings, in which.

DETAILED DESCRIPTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
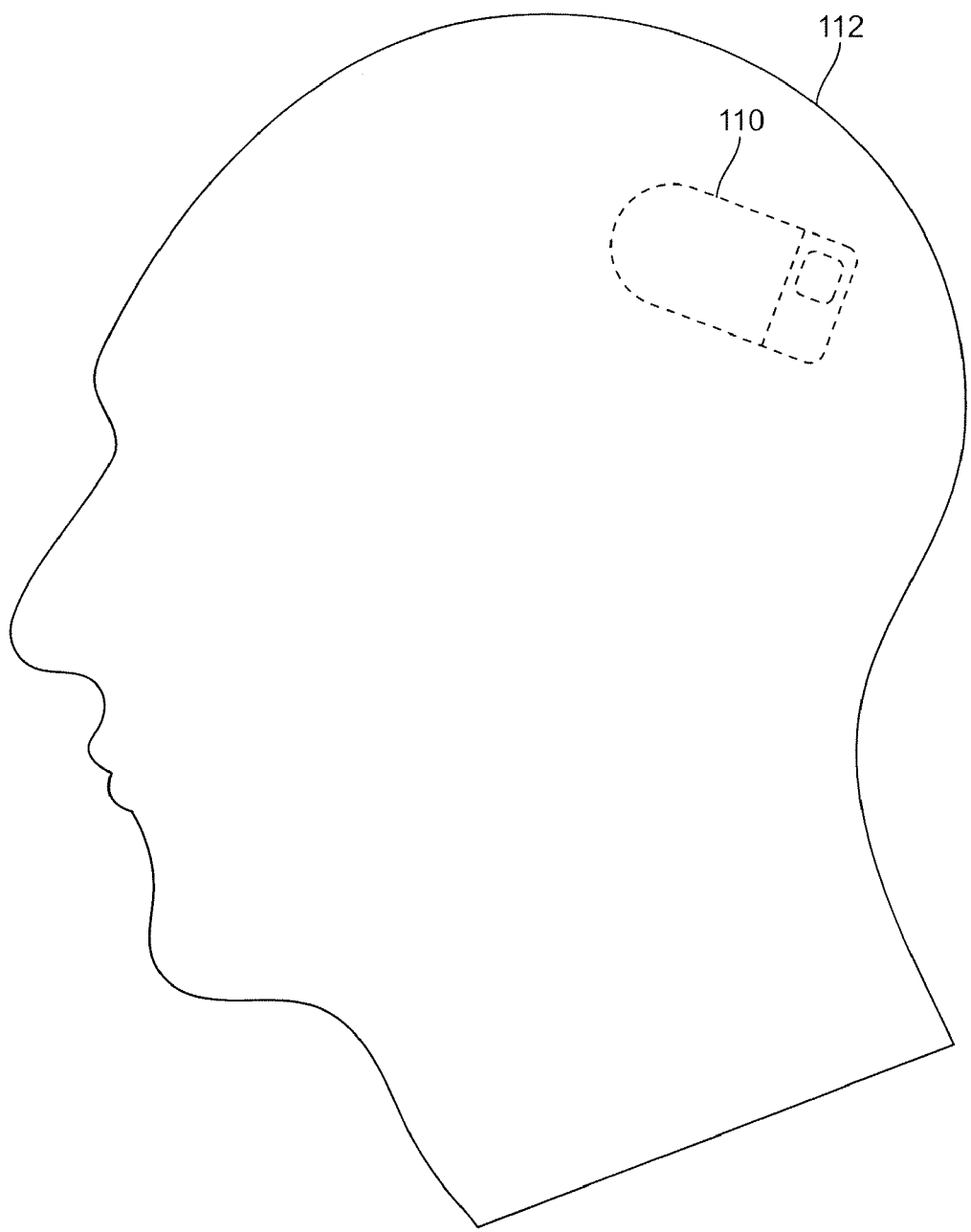
FIG. 1 is a schematic illustration of a patient's head showing the placement of an implantable neurostimulator according to an embodiment of the invention.

FIG. 1 depicts an intracranially implanted neurostimulator device 110 according to the invention, which in one embodiment is a small self-contained responsive neurostimulator located under the patient's scalp 112. As the term is used herein, a responsive neurostimulator is a device capable of detecting or anticipating neurological events such as ictal activity, and providing therapy to neural tissue in response to that activity, where the therapy is specifically intended to terminate the ictal activity, treat a neurological event, prevent an unwanted neurological event from occurring, or lessen the severity, frequency or likelihood of certain symptoms of a neurological disorder. As disclosed herein, the responsive neurostimulator detects ictal activity by systems and methods according to the invention.

Preferably, an implantable device according to the invention is capable of detecting or anticipating any kind of neurological event that has a representative signature. Examples of such signatures may include a condition of a signal related to a specific waveshape, spectral composition, topological distribution with respect to timing, strength or other features; and the signal can be derived from one or more electrical, chemical, or other sensors. While the disclosed embodiment is described primarily as responsive to epileptic seizures, it should be recognized that it is also possible to respond to other types of neurological disorders, such as movement disorders (e.g., the tremors characterizing Parkinson's disease), migraine headaches, chronic pain, and neuropsychiatric disorders such as schizophrenia, obsessive-compulsive disorders, and depression. Preferably, neurological events representing any or all of these afflictions can be detected when they are actually occurring, in an onset stage, or as an anticipatory precursor before clinical symptoms begin.

Figure 2:
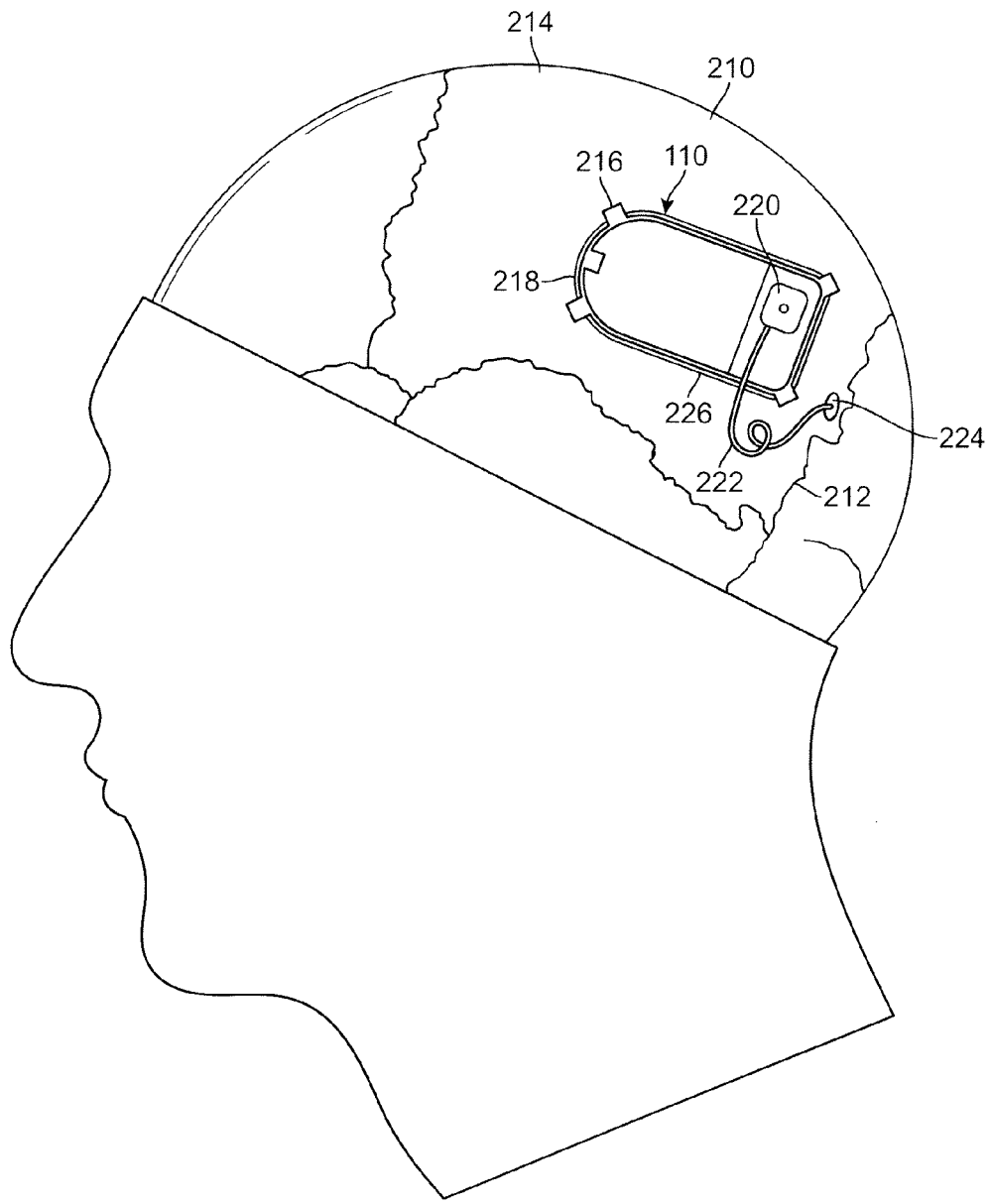
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoid suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patient's scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizures or their onsets or precursors, preventing and/or terminating such epileptic seizures, and responding to clusters of therapies as described herein.

In an alternative embodiment of the invention, the device 110 is not a responsive neurostimulator, but is an apparatus capable of detecting neurological conditions and events and performing actions in response thereto. The actions performed by such an embodiment of the device 110 need not be therapeutic, but may involve data recording or transmission, providing warnings to the patient, providing information to an external device, or any of a number of known alternative actions. Such a device will typically act as a diagnostic device when interfaced with external equipment, as will be discussed in further detail below.

The device 110, as implanted intracranially, is illustrated in greater detail in FIG. 2. The device 110 is affixed in the patient's cranium 214 by way of ferrule 216. The ferrule 216 is a structural member adapted to fit into a cranial opening, attach to the cranium 214, and retain the device 110.

To implant the device 110, a craniotomy is performed in the parietal bone 210 anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (e.g., one of the outputs 412-418 of FIG. 4, in an embodiment in which the outputs are implemented as depth electrodes) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell et al., Means and Method for the Placement of Brain Electrodes, issued Dec. 21, 1999, which is hereby incorporated by reference as though set forth in full herein, the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communication between the device 110 and external devices. Other portions of a system according to the invention may also be positioned outside of the housing 226, as will be described in further detail below.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws: only the fasteners retaining the device 110 in the ferrule 216 need to be manipulated.

Figure 3:
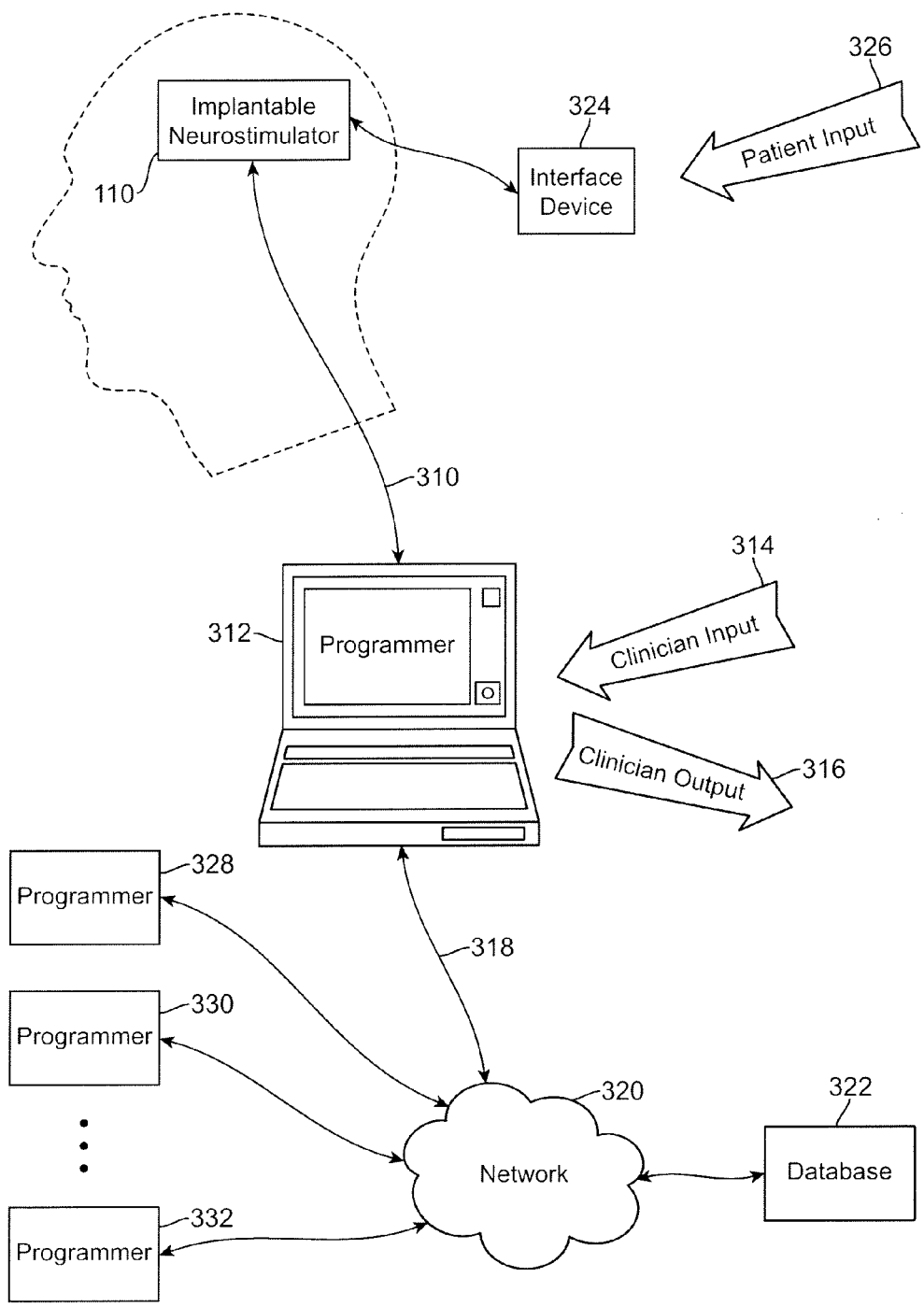
FIG. 3 is a block diagram illustration a system context in which an implantable neurostimulator according to the invention is implanted and operated.

As stated above, and as illustrated in FIG. 3, a neurostimulator according to the invention operates in conjunction with external equipment. The implantable neurostimulator device 110 is mostly autonomous (particularly when performing its usual sensing, detection, and stimulation capabilities), but preferably includes a selectable part-time wireless link 310 to external equipment such as a programmer 312. In the disclosed embodiment of the invention, the wireless link 310 is established by moving a wand (or other apparatus) having communication capabilities and coupled to the programmer 312 into communication range of the implantable neurostimulator device 110. The programmer 312 can then be used to manually control the operation of the device, as well as to transmit information to or receive information from the implantable neurostimulator 110. Several specific capabilities and operations performed by the programmer 312 in conjunction with the device will be described in further detail below.

The programmer 312 is capable of performing a number of advantageous operations in connection with the invention. In particular, the programmer 312 is able to specify and to set variable parameters in the implantable neurostimulator device 110 to adapt the function of the device to meet the patient's needs, upload or receive data (including but not limited to stored EEG waveforms, parameters, or logs of actions taken) from the implantable neurostimulator device 110 to the programmer 312, download or transmit program code and other information from the programmer 312 to the implantable neurostimulator 110, or command the implantable neurostimulator 110 to perform specific actions or change modes as desired by a user operating the programmer 312. To facilitate these functions, the programmer 312 is adapted to receive clinician input 314 (for example, programming and settings) and provide clinician output 316 (for example, information on the status of the neurostimulator); data is transmitted between the programmer 312 and the implantable neurostimulator device 110 over the wireless link 310.

The programmer 312 may also be equipped to receive external measurements 317 from other equipment, not shown. For example, various items of hospital equipment in an inpatient setting (such as an EKG monitor, a near-infrared spectroscopy (NIRS) monitor, or other equipment) or other personal equipment handled by the patient (such as a Holter monitor or wearable seizure counter, to give two examples) may also upload measurements 317 to the programmer 312, either in real time or periodically.

The programmer 312 may be used at a location remote from the implantable neurostimulator 110 if the wireless link 310 is enabled to transmit data over long distances. For example, the wireless link 310 may be established by a short-distance first link between the implantable neurostimulator device 110 and a transceiver, with the transceiver enabled to relay communications over long distances to a remote programmer 312, either wirelessly (for example, over a wireless computer network) or via a wired communications link (such as a telephonic circuit or computer network).

The programmer 312 may also be coupled via a communication link 318 to a network 320 such as the Internet. This allows any information uploaded from the implantable neurostimulator device 110, as well as any program code or other information to be downloaded to the implantable neurostimulator device 110, to be stored in a database 322 at one or more data repository locations (which may include various servers and network-connected programmers like the programmer 312). This would allow a patient (and the patient's physician) to have access to important data, including past treatment information and software updates, essentially anywhere in the world where there is a programmer (like the programmer 312) and a network connection. Alternatively, the programmer 312 may be connected to the database 322 over a transtelephonic link.

In yet another alternative embodiment of the invention, the wireless link 310 from the implantable neurostimulator 110 may enable a transfer of data from the neurostimulator 110 to the database 322 without any involvement by the programmer 312. In this embodiment, as with others, the wireless link 310 may be established by a short-distance first link between the implantable neurostimulator 110 and a transceiver, with the transceiver enabled to relay communications over long distances to the database 322, either wirelessly (for example, over a wireless computer network) or via a wired communications link (such as transtelephonically over a telephonic circuit, or over a computer network).

In the disclosed embodiment, the implantable neurostimulator 110 is also adapted to receive communications from an interface device 324, typically controlled by the patient or a caregiver. Accordingly, patient input 326 from the interface device 324 is transmitted over a wireless link to the implantable neurostimulator device 110; such patient input 326 may be used to cause the implantable neurostimulator device 110 to switch modes (on to off and vice versa, for example) or to perform an action (e.g., store a record of EEG data). Preferably, the interface device 324 is able to communicate with the implantable neurostimulator 110 through the communication subsystem 430 (FIG. 4), and possibly in the same manner as the programmer 312 does. The link may be unidirectional (as with a magnet and GMR sensor as described below), allowing commands to be passed in a single direction from the interface device 324 to the implantable neurostimulator 110, but in an alternative embodiment of the invention is bi-directional, allowing status and data to be passed back to the interface device 324. Accordingly, the interface device 324 may be a programmable PDA or other hand-held computing device, such as a Palm®, PocketPC®, or Windows Mobile® device. However, a simple form of interface device 324 may take the form of a permanent magnet, if the communication subsystem 430 is adapted to identify magnetic fields and interruptions therein as communication signals.

In various embodiments of the invention, the interface device 324 may also include additional functions. In one embodiment, the interface device 324 may include an alert capability, enabling the neurostimulator device 110 to transmit an alert to the interface device 324 to provide a warning or other information to the patient. The interface device 324 may also include therapy functions, including but not limited to transcranial magnetic stimulation (TMS) capabilities. Such therapy functions may be controlled by the neurostimulator device 110, the interface device 324 itself, or some other device on the network 320.

The implantable neurostimulator device 110 (FIG. 1) generally interacts with the programmer 312 (FIG. 3) as described below. Data stored in the memory subsystem 526 (FIG. 5) can be retrieved by the patient's physician through the wireless communication link 310, which operates through the communication subsystem 430 of the implantable neurostimulator 110. In connection with the invention, a software operating program run by the programmer 312 allows the physician to read out a history of sensed data. This history can include detected neurological events and EEG, perfusion, or other information from before, during, and after each neurological event. The history can also include specific information relating to the detection of each neurological event, or summary information and statistics describing the history and its trends. The programmer 312 also allows the physician to specify or alter any programmable parameters of the implantable neurostimulator 110. The software operating program of the programmer 312 also includes tools for the analysis and processing of recorded EEG records to assist the physician in developing optimized seizure detection parameters for each specific patient.

In an embodiment of the invention, the programmer 312 is primarily a commercially available PC, laptop computer, or workstation having a CPU, a keyboard, mouse and display, and running a standard operating system such as Microsoft Windows®, Linux®, Unix®, or Apple Mac OS®. It is also envisioned that a dedicated programmer apparatus with a custom software package (which may or may not use a standard operating system) could be developed. The programmer 312 can also be embodied into a specialized microchip, which can reside on a device which is plugged into a computer, for example, via a USB port.

When running a computer workstation software operating program, the programmer 312 can process, store, play back and display the patient's EEG signals, which were previously stored by the implantable neurostimulator 110 of the implantable neurostimulator system. The programmer 312 can also send the data or produce an alarm warning that can be sent, for example, over the Internet or to the pager device of a physician.

As described in U.S. Pat. No. 6,810,285 to Pless et al. for "Seizure Sensing Device and Detection Using an Implantable Device," issued Oct. 26, 2004 (which is hereby incorporated by reference as though set forth in full), the computer workstation software operating program also has the capability to stimulate the detection and anticipation of neurological events such as epileptiform activity or neural correlates of migraine. With real or fabricated electrographic (or other sensor) data, the workstation operating program can show, given a set of detection parameters, whether an event of interest would have been identified in the data. Furthermore, the software operating program of the present invention has the capability to allow a clinician to create or modify a patient-specific collection of information comprising, in one embodiment, algorithms and algorithm parameters for event detection.

The patient-specific collection of sensed information and subsequent responsive therapy deliveries, may be encoded into control laws. By identifying a condition of the signal related to the disorder, as will occur when detection includes the generation of one or more of a score, probability, or index, related to a characteristic of the detected event, the detection method can indicate a specific parameter of the stimulation signal which is to be varied, or set at a specific value, in the provision of treatment. In general, some characteristic or condition of detected activity may vary an output or therapy of the system; this is accomplished through the control laws. Treatment parameters that are used to determine therapy output according to control laws may be based upon the brain's response to a previously delivered stimulation signal or may be based upon ongoing activity, unrelated to a stimulation episode, which is sensed by one or more sensors. Each sensor can be configured to sense a particular characteristic indicative of a neurological or psychiatric condition, for example, a decrease in perfusion level that has been shown to be related to seizure initiation. The neural modulation signals of the therapy output can include any control signal that augments, attenuates, or inhibits cellular activity in a manner that normalizes or otherwise alters perfusion levels in a desired manner. In the above example, the neurostimulator will augment brain activity to increase perfusion. The neurological control system can evaluate the neural response or ongoing neural activity, via sensor feedback, in relation to the neurological disease state (where abnormal perfusion is defined as the disease state). The effective response to therapy may serve as a guide to the adjustment of stimulation according to control laws, which is used in subsequent therapy, where the determination of treatment parameters is guided by a positive or negative outcome of the prior therapy in relation to decreasing the disease state.

For example, control laws may produce an increased stimulation level in response to a sensed signal when the sensed signal indicates decreased perfusion. This is an example of a proportional control law which happens to be inversely related to the sensed parameter. Further, according to the control law program, the stimulation may only be increased to a certain level before alternative therapy is provided. The alternative therapy may include changing the stimulation signal rather than simply increasing the power of the signal since this did not produce a desired effect. The alternative therapy may also include stimulation at additional leads with the same control signal, since stimulation at a particular lead did not provide adequate changes in the sensed data with respect to normalizing the disease state. The values of parameters which are realized by the control laws can be modified in an automatic manner. For example, the evaluation of the disease state which is monitored as therapy progresses can also be monitored as treatment parameters are automatically varied. The control settings which result in one or more minimum values in disease state vector can be selected to provide an improved set of stimulation parameters during subsequent treatment. The set of disease state vectors which result from different stimulation parameters can be represented as a stimulation-and-disease-state transfer function, where the input stimulation is charted in relation to the output of the system which is sensed by the sensors. One or more (local) maxima of the transfer function, which can represent maximum increase(s) in blood flow, can then be selected as the parameters utilized by the control laws used during treatment. Accordingly, the invention can be realized as a brain modulation system which treats disease states by providing a stimulation signal that has parameters, such as intensity, that may be varied. The stimulation produced by the control laws can produce excitatory or inhibitory stimulation, or both, at different sites. In order to increase the stability of both control dictated stimulation and the transfer function used for evaluating control law parameters, the control laws can utilize averaging and integrating routines which dampen the rate of stimulation adjustment. This may be important when the optically sensed signals suffer from low SNR (signal-to-noise) levels, or tend to fluctuate considerably and wherein it is the overall mean increase or decrease in perfusion level which is related to the provision of therapy. Additionally, in order to increase the stability of providing control stimulation in response to a sensed signal, the control law circuit or control program which provides the feedback control can utilize operational integrators as well as differentiators (e.g., for slope or variance calculations) within the control law to create dampened proportional and integrated signals.

The patient-specific collection of detection algorithms and parameters used for neurological activity detection according to the invention will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator. In the disclosed embodiment of the invention, the patient-specific template includes information about the parameters needed to identify clusters of events, including the duration of the interval within which these events much occur, as will be described in further detail below.

Following the development of a patient-specific template in the programmer 312, the patient-specific template would be downloaded through the communications link 310 from the programmer 312 to the implantable neurostimulator 110.

The patient-specific template is used by the detection subsystem 522 and the CPU 528 (FIG. 5) of the implantable neurostimulator 110 to detect neural events in the patient's data. The patient-specific templates can detect events, such as epileptiform activity, within the patient's EEG (and other sensed) signals, and can be programmed by a clinician to result in responsive stimulation of the patient's brain, as well as the storage of data recorded before and after the detection, facilitating later clinician review.

Preferably, the database 322 is adapted to communicate over the network 320 with multiple programmers, including the programmer 312 and additional programmers 328, 330, and 332. It is contemplated that programmers will be located at various medical facilities and physicians' offices at widely distributed locations. Accordingly, if more than one programmer has been used to upload EEG records from a patient's implantable neurostimulator 110, the EEG records will be aggregated via the database 322 and available thereafter to any of the programmers connected to the network 320, including the programmer 312.

Figure 4:
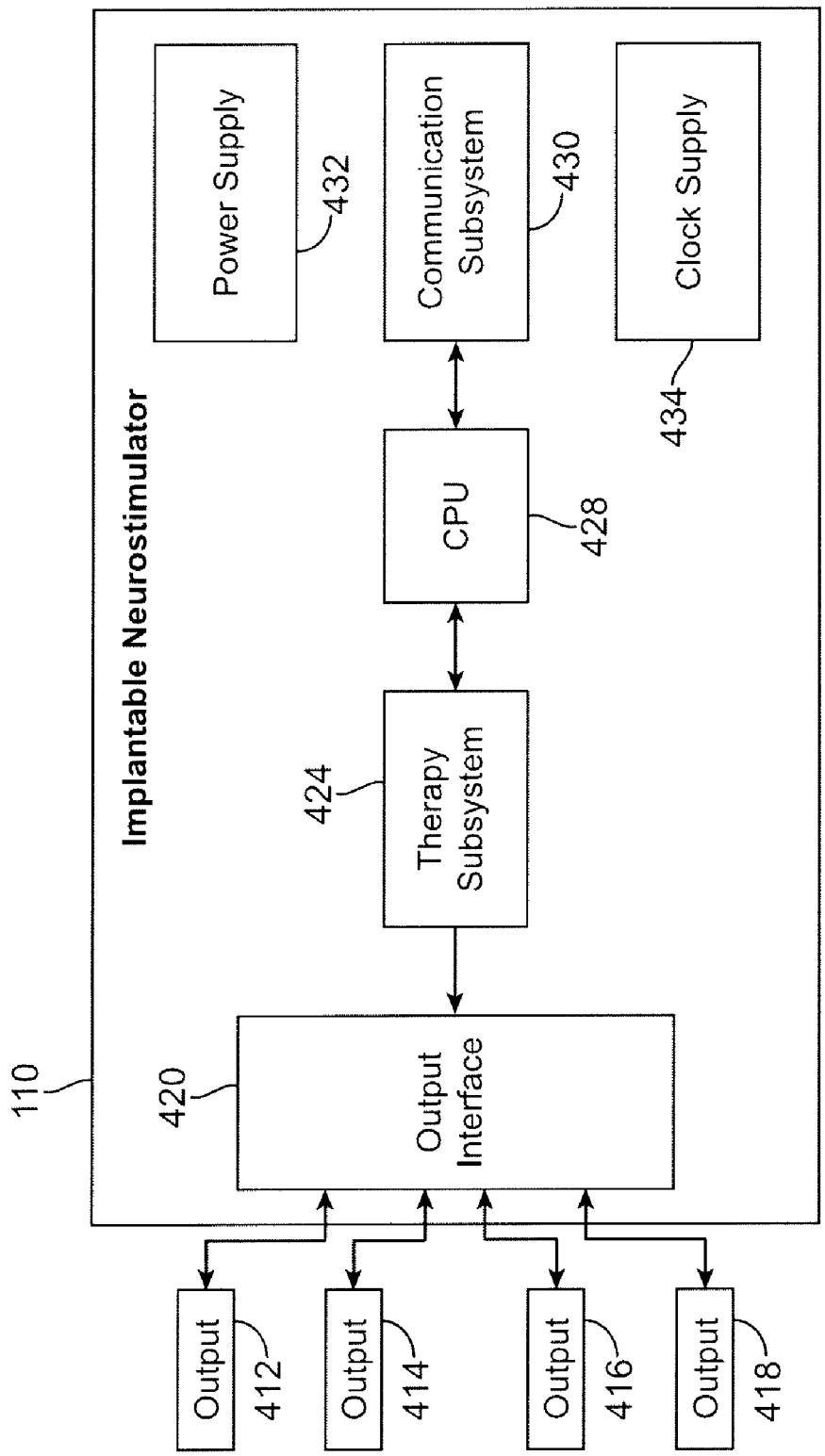
FIG. 4 is a block diagram illustrating the major functional subsystems of an implantable cerebral blood flow modulation device according to the invention.

FIG. 4 depicts a schematic block diagram of a stimulator system according to the invention, including an embodiment of the implantable neurostimulator device 110 comprising a small, self-contained, externally programmable and controlled stimulator that is intracranially implanted.

FIG. 4 is an overall block diagram of the implantable stimulator device 110 used to modulate cerebral blood flow according to the invention. Inside the housing of the neurostimulator device 110 are several subsystems making up the device. The implantable stimulator device 110 is capable of being coupled to a plurality of outputs 412, 414, 416, and 418 for various types of stimulation as described herein. In the illustrated embodiment, the coupling is accomplished through an interface such as a lead connector. The described embodiment is adapted to be used in an implanted environment to modulate a patient's cerebral perfusion for the treatment of epilepsy or other neurological disorders.

The outputs 412-418, each of which may be configured to provide electrical, magnetic, chemical, thermal or other types of stimulation to the patient's body, head, or brain, or are otherwise advantageously located near locations of interest in the patient's brain, where perfusion is desired to be modulated, or from which other areas of the brain may be modulated. Each of the outputs 412-418 is functionally coupled to an output interface 420 (this includes communication with remote stimulation devices that interact with the stimulator).

The therapy subsystem 424, which is coupled to the output interface 420, is capable of applying electrical and various other types of stimulation signals to tissue through the outputs 412-418. This can be accomplished in any of a number of different manners. For example, with electrical stimulation, it may be advantageous in some circumstances to provide stimulation in the form of a substantially continuous stream of pulses, or on a scheduled basis. It is contemplated that the parameters of the stimulation signal (e.g., frequency, duration, waveform) provided by the therapy subsystem 424 would be stored in this subsystem, but could also be adjusted or specified by other subsystems in the implantable device 110, and may be received from external equipment such as the programmer 312, as will be described in further detail below.

In accordance with the invention, the therapy subsystem 424 may also provide for other types of stimulation, besides the electrical stimulation described above. In particular, in certain circumstances, it may be advantageous to provide audio, visual, or tactile signals to the patient, to provide somatosensory electrical stimulation to locations other than the brain, or to deliver a drug or other therapeutic agent (either alone or in conjunction with stimulation). The provision of these other types of stimulation can occur via the external programmer 312.

Also in the implantable neurostimulator device 110 is a CPU 428, which can take the form of a microcontroller. The CPU 428 is capable of coordinating the actions of the device 110 and providing different therapies on different schedules (and at different locations) to the outputs 412-418 via the output interface 420, all according to programming and commands received from the programmer 312 and the patient interface device 324 (FIG. 3). For example, the CPU 428 may have a library of stimulation programs, evaluation algorithms, control laws, models, and other components that can be selected by the programmer 312.

Also provided in the implantable neurostimulator device 110, and coupled to the CPU 428 is a communication subsystem 430. The communication subsystem 430 enables communication between the device 110 and the outside world, particularly the external programmer 312 and the patient interface device 324, both of which are described above with reference to FIG. 3, and are used with the disclosed embodiment to command and program the device 110. As set forth above, the disclosed embodiment of the communication subsystem 430 includes a telemetry coil (which may be situated outside of the housing of the implantable neurostimulator device 110) enabling transmission and reception of signals, to or from an external apparatus, via inductive coupling. Alternative embodiments of the communication subsystem 430 could use an antenna for an RF link or an audio transducer for an audio link. Preferably, the communication subsystem 430 also includes a GMR (giant magnetoresistive effect) sensor to enable receiving simple signals (namely the placement and removal of a magnet) from a patient interface device; this capability can be used to initiate EEG recording as will be described in further detail below.

If the stimulation subsystem 424 includes the audio capability set forth above, rather than the communication subsystem 430, it may be advantageous for the communication subsystem 430 to cause the audio signal to be generated by the stimulation subsystem 424 upon receipt of an appropriate indication from the patient interface device (e.g., the magnet used to communicate with the GMR sensor of the communication subsystem 430), thereby confirming to the patient or caregiver that a desired action will be performed, e.g., that an EEG record will be stored.

Additional subsystems in the implantable neurostimulator device 110 are a power supply 432 and a clock supply 434. The power supply 432 supplies the voltages and currents necessary for each of the other subsystems. The clock supply 434 supplies substantially all of the other subsystems with any clock and timing signals necessary for their operation, including a real time clock signal to coordinate programmed and scheduled actions.

Figure 5:
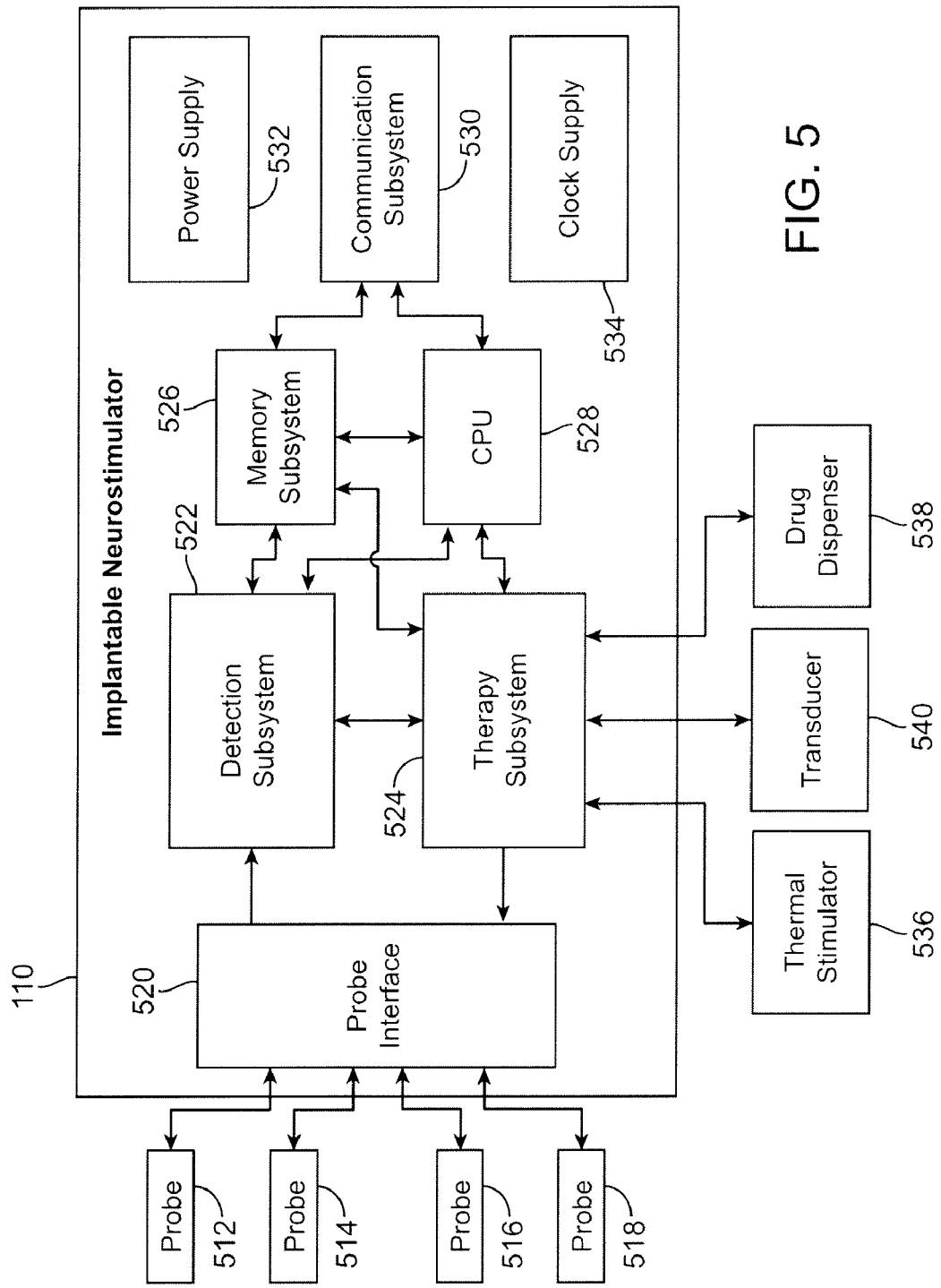
FIG. 5 is a block diagram illustrating the major functional subsystems of an implantable responsive blood flow modulation device according to the invention.

FIG. 5 depicts a schematic block diagram of an implantable responsive neurostimulator system according to the invention. The embodiment illustrated in FIG. 5 includes the capabilities of the programmable stimulator described with reference to FIG. 4, and is capable of acting responsively asset forth below. As the term is used herein, a responsive neurostimulator is a device capable of detecting neurological events (or other undesired activity) and delivering therapy in response to that activity. Therapy can include electrical stimulation specifically intended to terminate the undesired activity, treat a neurological event, prevent an unwanted neurological event from occurring, or lessen the severity or frequency of certain symptoms of a neurological disorder. It will be recognized that various other types of therapy, including especially the modulation of perfusion in and around certain structures of the brain, may also be delivered.

It should be recognized that the embodiment of the device described and illustrated herein is preferably a responsive neurostimulator for detecting and treating epilepsy by detecting seizure precursors and preventing and/or terminating epileptic seizures. It will be recognized, and it is described elsewhere herein, that similar methods and devices may be used to detect other types of events and to treat other neurological disorders as well.

FIG. 5 is an overall block diagram of the implantable neurostimulator device 110 used for measurement, detection, and treatment according to the invention. Inside the housing of the neurostimulator device 110 are several subsystems making up the device. The implantable neurostimulator device 110 is capable of being coupled to a plurality of probes 512, 514, 516, and 518. Each probe may be individually or jointly connected to the implantable neurostimulator device 110 via one or more leads, or may communicate remotely with the probe interface when the probes have their own power sources and communication telemetry, in order to achieve sensing and stimulation. In the illustrated embodiment, the coupling is accomplished through a lead connector. Although four probes are shown in FIG. 5, it should be recognized that any number is possible, and in the embodiment described in detail herein, eight electrodes on two leads are used. In fact, it is possible to employ an embodiment of the invention that uses a single lead with at least two electrodes, or two leads each with at least a single electrode (or with a second electrode provided by a conductive exterior portion of the housing in one embodiment), although bipolar sensing between two closely spaced electrodes on a lead is preferred to minimize common mode signals including noise.

Certain capabilities of the system may be realized using a micro-stimulator such as a BION®, which communicates with or incorporates the additional sensing methods and systems described herein to be responsive to different perfusion states. The system can also be realized by a network of micro-stimulators which provide sensing and/or stimulation in different regions of the brain and which may communicate with each other or a programmer 312 via telemetry or via physical connections. The coordination of such a network to provide cooperative stimulation using the multiple implanted micro-stimulators can be achieved by the programmer 312 and also by an implanted controller that coordinates the operation of the multiple stimulators.

The probes (for example, electrodes) 512-518 are in contact with the patient's brain or are otherwise advantageously located to sense signals or provide electrical stimulation. Each of the probes 512-518 is also electrically coupled to a probe interface 520. Preferably, the probe interface 520 is capable of selecting each electrode (or other sensor or probe) as required for sensing and stimulation; accordingly, the probe interface 520 is coupled to a detection subsystem 522 and a stimulation subsystem 524 (corresponding to the therapy subsystem 424 in FIG. 4). In one embodiment, the probes can be partially coated and can perform in-vivo voltammetry in order to assess neurotransmitter levels. In another embodiment, the stimulation/therapy subsystem may provide therapy and have outputs other than electrical stimulation, as described below. The electrode interface may also provide any other features, capabilities, or aspects, including but not limited to amplification, isolation, and charge-balancing functions, that are required for a proper interface with neurological tissue and not provided by any other subsystem of the device 110.

The detection subsystem 522 includes and serves primarily as a cerebral blood flow and EEG waveform analyzer; detection is accomplished in conjunction with a central processing unit (CPU) 528. The analysis functions are adapted to receive signals from the probes 512-518, through the probe interface 520, and to process those signals to identify neurological activity indicative of events such as seizures or precursors to a seizure. One way to implement EEG analysis functionality is disclosed in detail in U.S. Pat. No. 6,016,449 to Fischell et al. for "System for Treatment of Neurological Disorders," issued Jan. 18, 2000, incorporated by reference above. Additional inventive methods are described in U.S. Pat. No. 6,810,285 to Pless et al. for "Seizure Sensing and Detection Using an Implantable Device," issued Oct. 26, 2004, of which some details will be set forth below (and which is also incorporated by reference as though set forth in full). The detection subsystem may optionally also contain further sensing and detection capabilities, including but not limited to parameters derived from other physiological conditions (such as electrophysiological parameters, temperature, blood pressure, oxygen saturation, etc.). In general, prior to analysis, the detection subsystem performs amplification, analog to digital conversion, and multiplexing functions on the signals in the sensing channels received from the probes 512-518.

The therapy subsystem 524 is capable of applying electrical and other types of stimulation to neurological tissue through the probes 512-518, to the extent such probes are capable of applying stimulation. This can be accomplished in any of a number of different manners. For example, it may be advantageous in some circumstances to provide electrical or other stimulation in the form of a substantially continuous stream of pulses, or on a scheduled basis. Preferably, therapeutic stimulation is provided in response to abnormal neurological events detected by the EEG analyzer function of the detection subsystem 522 and to modulate cerebral blood flow as described herein. The EEG analyzer function of the detection subsystem 522 can utilize modules of the perfusion analyzer subsystem, which identify different conditions related to blood profile including flow, volume, gas content, and other aspects: this may advantageously contextualize activity analyzed by the EEG analyzer. The output of the detection subsystem can be fed to control laws in order to provide the stimulation signal. As illustrated in FIG. 5, the therapy subsystem 524 and the analysis functions of the detection subsystem 522 are in communication; this facilitates the ability of the therapy subsystem 524 to provide responsive stimulation as well as an ability of the detection subsystem 522 to blank the amplifiers while electrical stimulation is being performed to minimize stimulation artifacts. It is contemplated that the parameters of the stimulation signal (e.g., frequency, duration, waveform) provided by the therapy subsystem 524 would be specified by other subsystems in the implantable device 110 (for example, waveforms stored in the memory subsystem 526), as will be described in further detail below.

In accordance with the invention, the therapy subsystem 524 may also provide for other types of stimulation, besides the electrical stimulation described above. Such stimulation may be provided through the probes 512-518, or alternative therapy outputs may be provided, such as a thermal stimulator 536, a drug dispenser 538, or an audio or electromechanical transducer 540, which may be adapted for placement in, on, or near the brain, or elsewhere. The transducer 540 can provide tactile stimulation or pressure according to a signal, to areas of the brain or body; it has been observed that physical pressure can change neuronal activity. Selective amounts of focal pressure may be found to provide modulation of activity in a desired fashion. Cells are sensitive to mechanical stimuli, and actively respond through a variety of biological functions including migration, morphological changes, and alterations in gene expression and protein synthesis. Cell-distinct function (e.g., growth) or dysfunctional phenotypes (e.g., atherosclerosis and asthma) involve such mechanisms in response to specific biomechanical stimuli. To understand the cellular response to mechanical stress, numerous experiments have been conducted to apply a quantified mechanical stimulus to a single cell, and study its response. See, e.g., Tavalin S J et al., *Mechanical Perturbation of Cultured Cortical Neurons Reveals a Stretch-Induced Delayed Depolarization*, J. Neurophysiol. 1995. In particular, in certain circumstances, it may be advantageous to provide audio, visual or tactile signals to the patient, to provide somatosensory electrical stimulation to locations other than the brain, or to deliver a drug or other therapeutic agent (either alone or in conjunction with stimulation).

Also in the implantable neurostimulator device 110 is a memory subsystem 526 and the CPU 528, which can take the form of a microcontroller. The memory subsystem is coupled to the detection subsystem 522 (e.g., for receiving and storing data representative of sensed EEG signals and evoked responses), the therapy subsystem 524 (e.g., for providing stimulation waveform parameters to the therapy subsystem), and the CPU 528, which can control the operation of (and store and retrieve data from) the memory subsystem 526. In addition to the memory subsystem 526, the CPU 528 is also connected to the detection subsystem 522 and the therapy subsystem 524 for direct control of those subsystems.

Also provided in the implantable neurostimulator device 110, and coupled to the memory subsystem 526 and the CPU 528, is a communication subsystem 530 (corresponding to the communication subsystem 430 of FIG. 4). The communication subsystem 530 enables communication between the device 110 and the outside world, particularly the external programmer 312 and patient interface device 324, both of which are described above with reference to FIG. 3. As set forth above, the disclosed embodiment of the communication subsystem 530 includes a telemetry coil (which may be situated outside of the housing of the implantable neurostimulator device 110) enabling transmission and reception of signals, to or from an external apparatus, via inductive coupling.

The subsystems 524 and 530, and the power supply 532 and clock supply 534 provide the same benefits as corresponding components described earlier for FIG. 4.

It should be observed that while the memory subsystem 526 is illustrated in FIG. 5 as a separate functional subsystem, the other subsystems may also require various amounts of memory to perform the functions described above and others. Furthermore, while the implantable neurostimulator device 110 is preferably a single physical unit (i.e., a control module) contained within a single implantable physical enclosure, namely the housing described above, other embodiments of the invention might be configured differently. The neurostimulator 110 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described above may be performed by electronic hardware, computer software (or firmware), or a combination thereof. The division of work between the CPU 528 and the other functional subsystems may also vary: the functional distinctions illustrated in FIG. 5 may not reflect the partitioning and integration of functions in a real world system or method according to the invention.

Figure 6:
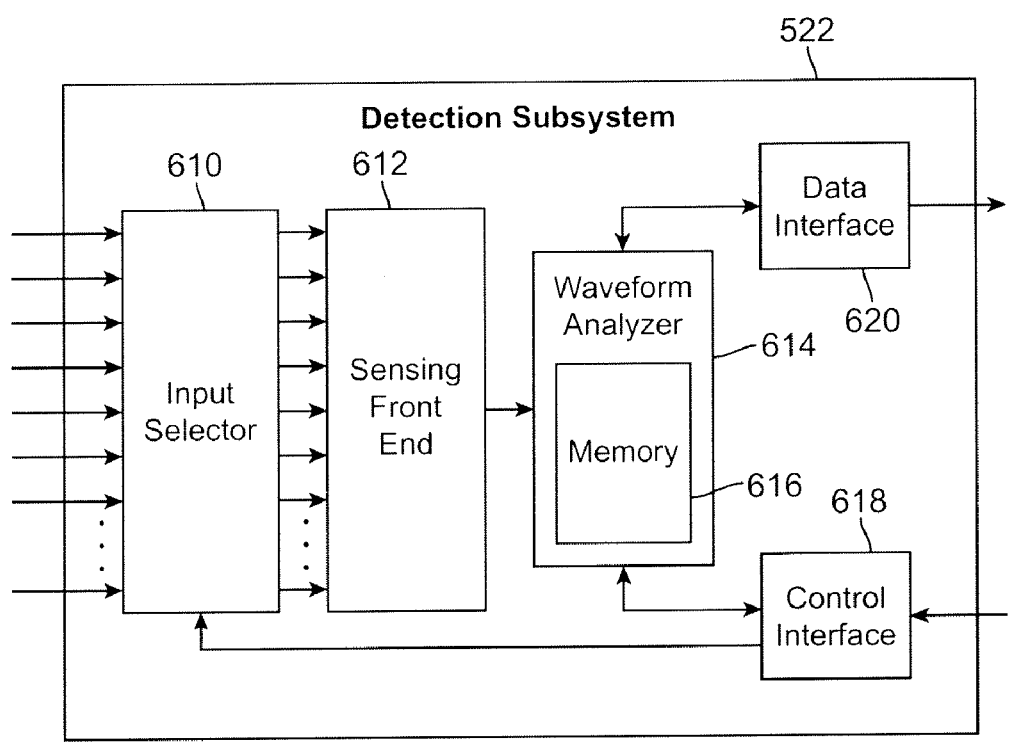
FIG. 6 is a block diagram illustrating the functional components of the detection subsystem of the implantable device shown in FIG. 4.

FIG. 6 illustrates details of one embodiment of the detection subsystem 522 (FIG. 5). Inputs from the probes 512-518 are on the left, and connections to other subsystems are on the right. The probes can be sensors which sense electrical patterns (e.g., electrodes), temperature, characteristics of blood, electrocardiogram, movement, posture, and other characteristics related to the patient or to the patient's activity, as are described elsewhere herein.

Signals received from the probes 512-518 (as routed through the probe interface 520) are received in an input selector 610. The input selector 610 allows the device to select which probes (for example, selected from the probes 512-518 of FIG. 5; it should be noted that the input selector 610 has eight inputs as illustrated) should be routed to which individual sensing channels of the detection subsystem 522, based on commands received through a control interface 618 from the memory subsystem 526 or the CPU 528 (FIG. 5). Preferably, for electrographic and impedance measurements, each sensing channel of the detection subsystem 522 receives a bipolar signal representative of the difference in electrical potential between two selectable electrodes. Accordingly, the input selector 610 provides signals corresponding to each pair of selected electrodes (of the probes 512-518) to a sensing front end 612, which performs amplification, analog to digital conversion, and multiplexing functions on the signals in the sensing channels.

A multiplexed input signal representative of all active sensing channels is then fed from the sensing front end 612 to a waveform analyzer 614. The waveform analyzer 614 is preferably a special purpose digital signal processor (DSP) adapted for use with the invention, or in an alternative embodiment, may comprise a programmable general purpose DSP. The waveform analyzer 614 contains modules for analyzing sensed data, such as an EEG analyzer function, a perfusion analyzer function, and a temperature analyzer function; these functions may be implemented in the same DSP with different programming, or may be implemented separately. In the disclosed embodiment, the waveform analyzer has its own scratchpad memory area 616 used for local storage of data and program variables when the signal processing is being performed. The signal processor performs suitable processing, measurement, and detection methods as described generally above and in greater detail below. Any results from such methods, as well as any digitized signals intended for storage transmission to external equipment, are passed to various other subsystems of the neurostimulator device 110, including the memory subsystem 526 and the CPU 528 (FIG. 5) through a data interface 620. Similarly, the control interface 618 allows the waveform analyzer 614 and the input selector 610 to be in communication with the CPU 528. The waveform analyzer can also combine information across sensors to evaluate data, detect events, and produce its results, and can accomplish pattern matching based upon templates and algorithms, apply control laws to create stimulation therapy, generate scores, probabilities, and indexes which reflect conditions of the sensed signals and guide the stimulation treatment.

The evaluation of the sensed signal, the evaluation of a reference value or criterion to which the sensed signal will be compared, or the comparison itself can be achieved by means of one or more of the following: a model, an algorithm; an equation; a transform (such as Hilbert, Fourier, or wavelet method); filtering; temporal analysis or time-frequency analysis which can be combined with spatial analysis; parametric and non-parametric statistics; multivariate and cluster analysis, including assessment by discriminant analysis or computation of Mahalanobis or Euclidean distance; factor or independent component analysis; phase or latency analysis; correlation/regression analysis; non-linear; fractal, and fuzzy logic analysis techniques and measures of chaos, complexity or entropy including Lyapunov exponents and Kolmogorov-Sinai. There are numerous other possibilities. The sensed signal can be related to an event, the time before or after an event, and can be a signal sensed in response to stimulation, can be signals sensed both before and after stimulation. The examples of spectral analysis, filtering, and component analysis given above may be related to the detection of the optical signal and the detection of patterns within the optical signal (and separating the signal from noise), however, wavelet or other time-frequency analysis can also be utilized in order to generate a spectrogram which may be analyzed in order to detect or remove periodicities within the sensed data. For example, fluctuations in the perfusion data related to heart rate can be removed, or compensated for, prior to evaluating the changes in the perfusion which occur within a sensed brain area. In any case, when evaluating the sensed optical data and comparing this to a referenced data set, some estimate of perfusion increase or decrease will be needed in order to guide the control law in providing treatment. For example, if an inferential statistic such as re-sampling (e.g., bootstrap) analysis is provided, then the histogram data can be divided into deciles (or other cumulative density function may be used). If a comparison of an estimate of the current sensed data with this reference dataset indicates that the current data is below some criteria (e.g., within the lower 2 deciles) then stimulation can be initiated and the magnitude of the stimulation can be proportionate to the results of the comparison. Alternatively, therapy may not be graded by degree of the sensed data and the therapy may simply be responsive to the detection of an event. For example, if optical data sensed at multiple leads is submitted to a multivariate equation, and the resulting score indicates that the probability of a disease state is at least 80%, then this can result in stimulation, regardless of the size of features which may exist in the sensed data. The multivariate equation may be a discriminant function which was previously derived using discriminant analysis on a training set of data which included data for which a medical professional determined a disease state existed, and data which was regarded by the medical professional as not being related to a disease state. When sensed data occurs across multiple modalities such as both optical and electrical, these measures can be normalized for the subject and combined into a disease state vector, which may be conceptualized and evaluated, as a Mahalanobis distance from an origin which is a desired treatment site. Accordingly, when the disease state vector increases in size then some parameter may be automatically increased or stimulation may be triggered in an attempt to decrease the size of this vector.

The sensed signal can be used to provide stimulation according to, for example, one or more models; algorithms; subroutines; equations; control laws, which may be rule-based and accomplished in series or in parallel, be guided by fuzzy logic, be guided by linear or non-linear rule sets, be guided according to a transfer, step, or other function; the result of a comparison of sensed data to reference data or threshold; a score, probability, or index; and the sensed data can be used to determine how, when, where, and what stimulation subsequently takes place. These rules, which would generally (but not necessarily) be computed offline, can be codified into one or more control laws for use in the implantable neurostimulator 110.

Figure 7:
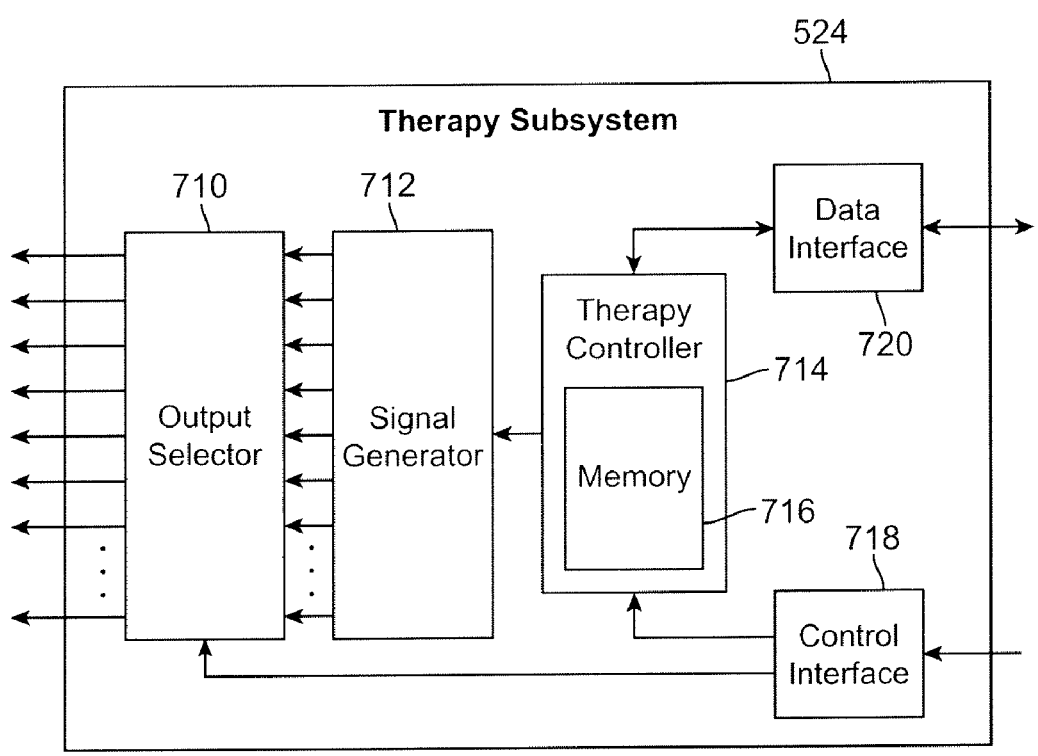
FIG. 7 is a block diagram illustrating the functional components of the therapy subsystem of the implantable device shown in FIG. 4.

FIG. 7 illustrates the components functionally present in an exemplary therapy subsystem 524 according to the invention. Through an output selector 710, the therapy subsystem 524 is capable of driving a number of outputs, including the thermal stimulator 536, the drug dispenser 538, and the audio transducer 540 illustrated in FIG. 5. Other outputs include leads for electrical stimulation and other stimulators as described in greater detail below with reference to FIGS. 8-11 and 13. Preferably, the output selector 710 is configured and may be programmed to drive more than one output, either in sequence or simultaneously.

The nature of the outputs is defined by a signal generator 712, advantageously designed to be able to produce different types of output signals for different types of outputs. For example, for electrical stimulation, biphasic pulsatile stimulation or low-frequency sine wave stimulation may be advantageous signals, whereas for a burst of thermal stimulation, a single-polarity longer-duration pulse signal may be more appropriate. Thermal stimulation can be provided using a heating element such as a resistor configured to be used with the electrical stimulation contacts. Alternatively, cooling may be desirable. When treating epilepsy by cooling, the cortical surface should not usually be cooled to lower than 20° C., but should be cooled to lower 26° C. for an appreciable antiepileptic effect to be gained. Small thermoelectric cooling devices, called Peltier devices, can be used to provide cooling. Cooling may be a particularly advantageous procedure when the epilepsy focus is in a language or primary motor area, since tissue stimulation, ablation, or resection may provoke disorders in behaviors controlled by these areas. For various forms of active sensing described in detail below (in which a physiological or other physical response to an applied stimulus is measured), signals generated by the signal generator 712 are preferably coordinated with measurements made by the detection subsystem 522 (FIG. 5).

Such coordination and control of the signal generator 712 is accomplished through a therapy controller 714, which may include memory 716 to "play back" therapy waveforms, to store parameters used to create waveforms, and for other purposes—such waveforms may also be received via a data interface 720 from the main memory subsystem 526 or the CPU 528. The therapy controller receives input from a control interface 718, which is coupled to the CPU 528, thereby allowing the CPU 528 to control both the therapy subsystem 524 and the detection subsystem 522. Through the control interface 718, the CPU 528 is also capable of controlling the application of therapy (or other stimulation) to a desired combination of outputs via the output selector 710.

FIGS. 8-13 illustrate several embodiments of probes advantageously usable in a system according to the invention to measure and modulate perfusion. The chronically implantable probes illustrated in FIGS. 8-13 are advantageously connected to a device 110 according to the invention, and in the illustrated embodiments, have distal ends generally 0.5-3 mm in diameter, are at least partially flexible, and are of a length sufficient to reach from the device 110 to a desired target. The illustrations are schematic in nature and are not to scale. The probes of FIGS. 8-13 are illustrated as generally cylindrical depth probes, capable of being positioned within the gray or white matter of a patient's brain, but it should be recognized that surface cortical probes are also advantageous in certain embodiments; the differences between the illustrated probes and their cortical counterparts would be known to a practitioner of ordinary skill, and would primarily entail a different (paddle-shaped) physical configuration at the distal end.

Figure 8:
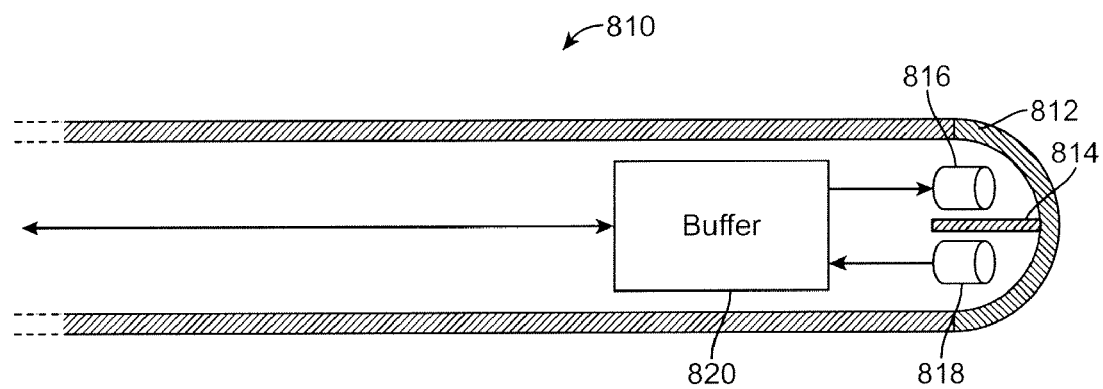
FIG. 8 is a schematic cutaway diagram of an optical sensing and stimulation probe according to the invention.

Referring now to FIG. 8, an optical probe 810 capable of measuring cerebral perfusion and applying optical stimulation is illustrated. The probe 810 includes an optically translucent distal tip 812 and opaque barrier 814 separating a light source 816 (typically one or more light emitting diodes, or LEDs) and a light sensor 818 (typically a photodiode, but it may also include a CCD or other light sensor). In the illustrated embodiment, the light source 816 and light sensor 818 are connected to a buffer 820, which in turn is coupled to the device 110. This configuration allows a single set of control wires (typically a pair) to both send information bi-directionally between the probe 810 and sensor 818; in this embodiment the probe interface 520 (FIG. 5) would perform the buffering functions otherwise provided by the buffer 820.

The optical probe 810 of FIG. 8 is advantageously used to measure perfusion via pulse oximetry methods. The disclosed embodiment is configured to measure reflected light; embodiments measuring transmissivity are also possible. The light source 816 includes two LEDs, for estimating both oxyhemoglobin $HbO_2$ and deoxyhemoglobin (HbR). For example, one red LED in the 600-750 nm range and an infrared LED in the 850-1000 nm range may be used, or in any case the wavelengths chosen are advantageously below and above approximately 805 nm, at which point the two chromophores are similarly absorbed (this is the hemoglobin isobestic point). To obtain a single measurement, the two LEDs are pulsed (preferably in sequence) and two corresponding measurements are obtained at the light sensor 818, which may be a photodiode. The light sensor 818 can be turned to a specific wavelength, or spectral analysis may be used to derive energy at a specified frequency, or, rather than performing spectral analysis, lock-in amplifiers can be used to obtain data for specific frequencies in the near-infrared spectrum. The ratio of red reflectivity to infrared reflectivity is calculated (by the detection subsystem 522 or the CPU 528). Preferably, multiple ratio measurements are obtained over the course of at least one heart beat to obtain a value for peak perfusion, typically be subtracting minimum values (baselines) from maximum values (maximum perfusion). The peak value is compared to a preprogrammed lookup table to obtain an oxygen saturation value; the contents of the lookup table would be routing to calculate for a practitioner of ordinary skill. It should be noted that different methods of near infrared spectroscopy (NIRS) techniques may be implemented as well, and may combine and utilize several different perfusion measures.

It will be noted that perfusion measurements obtained by the optical probe 810 are typically relevant only in comparison to previously obtained values of trends, as measurements may be affected over a long term by tissue growth and other physiological changes around the probe 810. As will be described in details below, systems and methods according to the invention use trends accordingly.

In an embodiment of the invention, the light source 816 is further operable to optically stimulate brain tissue, which may result in perfusion changes or other desired neurophysiological results. For purposes of measurement, however, it is preferable to operate the light source 816 with low amplitude, duration and other characteristics that are unlikely to cause undesired effects.

The optical probes may be placed in a number of different locations. The probes can be placed on the scalp, as can occur when an external device will communicate with implanted components of the system. This communication can occur using the programmer 312 which receives information from the external probes and sends this information to the implanted device 110. If sensors are located on the outside of the skill, MR image data can be used to derive a model (e.g., of the bone, brain, cerebrospinal fluid and muscle tissues), which accounts for transfer characteristics of intervening tissue, and which can be incorporated into an analysis of the optical data. An iterative-based method for improving localization in diffuse tomography reconstruction may be used, which is based upon the MRI data. Alternatively, and with some benefit, the probes are implanted in the patient and positioned on the dura, cortex, or in sub-cortical locations and structures. The probes can also be placed to sense from the arterial and venous passages of a region as may occur in order to determine the transfer function of oxygen utilization in a region of tissue.

Assessment of a disorder such as epilepsy, with respect to both sensing perfusion irregularities and also determination of probe placement, can be assisted by various imaging procedures. Regional Perfusion Imaging (RPI) is an MRI procedure that matches cerebral arteries to flow territories. RPI is designed to non-invasively provide standard perfusion and cerebral blood flow data, and determine the contribution of each artery as well as the role of collateral vessels. RPI is valuable in determining the etiology of cerebral ischemia with respect to a disorder, in identifying the supply vessels of capillary abnormalities and arteriovenous malformations, and in assessing the collateral flow in the case of stenosis. While many conventional methods (e.g., contrast-enhanced angiography) for visualizing the vascular trees that terminate from major cerebral arteries, and for assessing collateral flow, can also be used, these techniques are often invasive. Unlike RPI, these other methods do not provide comprehensive information about tissue perfusion. By placing the sensors on the relevant cerebral arteries and/or cerebral and cerebellar veins, as determined by RPI techniques, the functional perfusion of an area may be assessed in an improved manner. Of course, RPI can also be used to guide placement of stimulation devices when these are different from the probes, in order to provide improved therapy.

Several assumptions are often made in measures of CBF obtained using NIRS. For example, it may be assumed that cerebral metabolic rate, blood flow and/or volume remain constant during the short measurement interval. This may not be true, and further, many other factors produce considerable variation in the measurements. In order to increase the validity of the measurements, NIRS sensing and event detection can be limited to, or adjusted for, the patient's position, posture (e.g., supine), activity level, or other sensed characteristic, or even can be implemented only during certain times of day (e.g, when the patient is sleeping). The sensitivity to brain activation and oxygen levels, or more precisely, relative changes in brain activation, is often contaminated by several signals such as systemic physiological signals, which can account for a larger percent signal variation than that of the brain activation. In some cases, it has been observed that these other signals may even phase-lock with the stimulation, causing the optical signal measured centrally to detect changes related to both central and peripheral responses to stimuli.

Accordingly, NIRS data can be combined with, or measured in relation to, pulse oximetry, such as only measuring NIRS data at the peak of the EKG. Further, central NIRS data can be measured in the context of other measurement of arterial oxygen saturation ($SaO_2$), or other arterial gas estimations, measurements of transcutaneous oxygen and carbon dioxide, measures of systemic circulation as monitored by electrocardiograph and invasive or non-invasive blood monitors (e.g., blood pressure sensor, or flowmetry), in order to obtain a measurement of peripheral changes which can affect central NIRS readings. In other words NIRS data, and changes, can be evaluated relative to peripheral changes in order to provide more accurate sensing and decrease false alarms. For example, if a change in an NIRS measure occurs at a probe monitoring the brain, at a time close to a peripheral change in the cardiovascular measurements (factoring in, when appropriate, delays between the two sites), then such a change may be ignored, whereas in the absence of this change, the NIRS measure may indicate a cerebral event for which responsive neurostimulator is appropriate.

The invention can utilize circulation monitoring of both central and peripheral regions to permit measurement or inference of the general perfusion of the monitored tissue, in relation to manifestation or promotion of different neural disorders. Methods can include NIRS, various types of flowmetry, ultrasound velocity, and use of an electromagnetic or magnetic flowmeter in the measurement of voltage induced in a moving electroconductive liquid as it crosses the lines of a magnetic field, since this is directly proportional to the flow rate.

Recapitulating to some extent, then, an NIRS signal is analyzed relative to a cardiopulmonary event, such as a component of the EKG signal, or a peripheral measure such as instantaneous blood pressure or heart rate. Statistical and signal analysis procedures such as template matching and can be used to classify, score, or otherwise analyze the optical data. For example, the NIRS signal, or a transform of the NIRS signal, such as a frequency transform, can be analyzed over time using a principle component analysis (PCA) or an independent component analysis (ICA) to determine the principle spatial components of the spatial-temporal covariance of baseline NIRS data. This can then be used to filter systemic or evoked signal variation from subsequent brain NIRS activation data. In an embodiment, data from implantable sensors is collected for this analysis at least in part by the implantable neurostimulator device 110, which later transfers the data to the programmer 312 for combination with other data (e.g., data from a non-invasive NIRS unit) and for offline analysis. This approach is particularly useful to collect baseline data in an inpatient environment or on a time-limited outpatient basis. Further, temporal or spatiotemporal (or frequency and phase for frequency transformed data) PCA can also be used to analyze and classify the incoming signals relative to a baseline period, or a period that is indicative or a system of the disorder to be treated (e.g., during a seizure in the case of epilepsy). Additionally, post-processing of time series data taken by the NIRS can include analysis procedures which utilize multiple steps, each relating to the time or frequency domain. For example, clustering algorithms can assist in classification or segmentation of data, using linear or non-linear analysis, including fuzzy-logic schemes, applied to the time, time-frequency (e.g., wavelet outputs), or spectral data. Post stimulation data can also be assessed using these methods. For example, a level of excitation of brain tissue can be estimated by examining the hemodynamic response to a brief period of therapeutic stimulation compared to the perfusion profile prior to the stimulation. This can be used in a system according to the invention to assess therapeutic efficacy on an off-line basis using the programmer 312 or the database 320, thereby allowing the neurostimulator device 110 to be programmed with the most effective treatment regimen.

In embodiments of the invention, various useful measures and indices can be computed using NIRS. Regional cerebral oxygen saturation may be assessed by a tissue oxygen index (TOI). Brain absorption of the light signal is due to the main cerebral chromophores, which are oxyhemoglobin ($HbO_2$) deoxyhemoglobin (HbR), and oxidized cytochrome oxidase (CtOx). It has been shown that the $HbO_2$ and HbR measures are related directly to cellular activation. Increases in cerebral blood volume (CBV) tend to correlate with increases in $HbO_2$ and in HbR, which sum to equal Total Hb (or $Hb_{total}$ or $Hb_T$). These measurements are normally relative measurements with an arbitrary zero point, and the change is related to changes in CBV.

The conditions of the sensed NIRS signal can refer to the characteristics of the signal related to changes in these measures. The $HbO_2$ and HbR measurements can be assessed independently, or can be used in an index combining these measures in various useful ways. For example, $HbO_2$ and HbR measurements can be measured alone, or $HbO_2$+HbR can be assessed to provide $Hb_T$, or $HbO_2/(HbO_2+HbR)$ can reflect relative oxygen utilization as a function of blood flow. Hbdiff ($[HbO_2-HbR]$) is often used to track changes attributable to saturation alone. Small changes in $HbO_2$ concentration can be reflective of cerebral blood flow, remembering that the accumulation of $HbO_2$ in the brain is dependent on both arterial inflow and venous outflow. Regional cerebral oxygen saturation ($rSO_2$), may be derived from the ratio of $HbO_2$ to total hemoglobin $Hb_T$, which is a percentage value of $rSO_2$. NIRS methods can include diffuse optical imaging (DOI) techniques including diffuse optical tomography (DOT). Each sensor may have a source, or several sensors can absorb light from a relatively distal source, the amount absorbed being related to activation of the regions between the source and sensor.

While two wavelengths are often used to accomplish NIRS, additional wavelengths can also be relied upon. For example, the NIRO 300 (Hamamatsu Photonics KK, Hamamatsu, Japan) uses four wavelengths of near-infrared light (775, 825, 850, and 904 nm). The NIRO 300 sensor contains a laser diode and three detectors placed at 4 or 5 cm from the source of emitting light. Its TOI (%) measure is based upon the ratio of $HbO_2$ to $Hb_T$. Previous models of the NIRO only monitored changes in HbR concentration and the redox state of cytochrome oxidase with a modified Beer-Lambert Equation. The current NIRO also improves its measurements using a specially resolved spectrometer (SRS), which combines multidistance measurements of optical attenuation in order to estimate the absolute concentration of $HbO_2$ and HbR in the tissue, rather than relative concentrations. This is possible since the values derived by STS are not differentially altered by influences of diffusion. As per this variant of NIRS, the NIRS source can be generated continuously, can be modulated (e.g., pulsed), can be transmitted in sequential pulses, and can be responsively generated under certain conditions or at certain times. It will be recognized that while only certain spectral components and wavelengths are currently used for both the optical source and measurement, the invention can be expanded to other wavelengths that have been found to be useful in determining a perfusion profile. In an embodiment of the invention, measurements from a NIRO 300 or similar tool may be provided as external measurements 317 to the programmer 312, and used in combination with measurements from the implantable neurostimulator device 110 of the invention (including electrographic and optical measurements, to name two possibilities) to assess a patient's perfusion in areas of interest, either in baseline states or in an episode of epilepsy or other neurological disorder.

Accordingly, NIRS can provide both relative and absolute measures for a number of perfusion related attributes. While changes in measures are currently relied upon more frequently than absolute measures, with the advances in technology absolute measures are becoming more accurate, and additionally using implanted sensors rather than sensors attached to the scalp should increase the accuracy of measurement. The sensed signal obtained at one or more probes can be compared, for example, by being z-transformed, to either self or population normative data, or to both. Signal processing techniques can extract relevant features from the NIRS data and can compare these to templates, use these in control laws, submit these to algorithms, statistically compare normative data, or simply compare these to a threshold. The measured data can then be used to produce time series data, which can be analyzed using both temporal and spectral techniques which are able to identify conditions of the signal and provide event detection.

The analysis of the time series data can include assessment of temporal, spatial, and spatiotemporal patterns of activity as detected across multiple sensors. The signals can be assessed using techniques which are commonly applied to the analysis of biological data, including the slower responses of the Galvanic skin response, like the orienting response, which have similar durations to some of the hemodynamic responses measured in NIRS (e.g., from 2-6 seconds). For example, the area under the curve, rate of ascent, rate of descent, the duration or amplitude of the half-maximum value, for a measure such as $HbO_2$ level, can be assessed. When $HbO_2$ and HbR are both assessed, the difference between the two curves can be calculated. Because NIRS is able to measure hemodynamic, metabolic, and fast neuronal responses to brain activation, the analysis techniques chosen will depend on the biological process that is being assessed. The shortest available sampling time of one-half second in commercially available NIRS equipment has recently been shortened to ⅙ of a second, allowing observations of more rapidly changing phenomena. For example, changes in $HbO_2$ data may contain a heart beat component superposed upon signals which slowly change over time. Measurement of these slow components can be accomplished after filtering out the fast component(s), and measurement of the fast component(s) can be made by transforming the data into the frequency domain and then measuring the spectral power of the fast frequency(ies). A high frequency sampling rate permits NIRS to be effective for detecting physiological responses, transient changes activity, and activity which may be related to events such as external stimulation or manipulation. The lower speed sampling may have other advantages such as being characterized by lower noise levels. The sampling rate may be specified according to the purpose of the measurement.

An index of synchronization between different brain regions may also be used in the analysis of data such as NIRS data. It is not only important to identify the neural populations underlying the neural event but also to depict their temporal dynamics. This can be accomplished using various non-linear and linear methods of analysis and correlation analysis. For example, using a geometric method, a phase portrait can be derived to obtain a functional may of neural changes in oxygen saturation as measured by NIRS. A phase portrait can be generated by taking the signal of one location as a reference for the other locations like a Lissajous figure. Measuring synchronization using the shape of an ellipse in phase portrait has the advantage for physiological data that it can reflect neural dynamics in both space and time. Synchronization can also be examined using linear estimates of synchronization where these can be indexed by the deviation of the actual distribution of the phases from a uniform distribution, or the relative phases, in the case where the phases of components of two sensors are compared.

NIRS has certain advantages compared to other sensing modalities. For example, spatially-resolved NIRS can provide better localization capabilities than EEG, especially when sensed from the scalp, and can require less processing of the data in order to obtain this localization. Sensing of NIRS data can occur during the stimulation period since it is not subject to electrical artifact, as would be sensed EEG data. While $Hb_T$ provides a measure of the cerebral blood volume (CBV), the individual concentrations of the two forms of hemoglobin are determined by physiological characteristics such as regional blood volume, atrial/venous blood flow, and metabolic rate of oxygen consumption, which is related to cellular activity.

NIRS can be used not only to identify regions of activation, but also distributed networks within which types of activation, such as seizure, can occur. By using two or more sensors, located at different regions of a neural network, the relative activation of that network can be determined. Seizures do not simply propagate omnidirectionally, but are normally distributed across neural tissue that is functionally connected. NIRS data can assist to determine the most likely path of a seizure through the network and can therefore assist in determining where stimulation should take place, as well as evaluating the effects of the stimulation. NIRS data can also be used to categorize a type of neural event, such as permitting classification of seizure type, where different seizure types have been found to product different, sometime opposite, changes in NIRS measurements.

Figure 9:
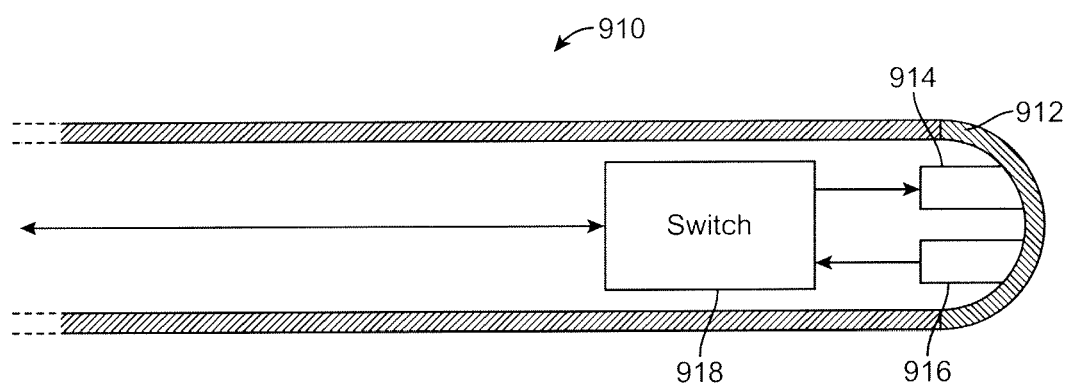
FIG. 9 is a schematic cutaway diagram of a thermographic sensing and stimulation probe according to the invention.

A thermal probe 910 is illustrated in FIG. 9; it is capable of measuring temperature. In one embodiment, cerebral perfusion can be measured by thermographic means. The thermal probe 910 includes a thermally conductive distal tip 912 (the shape of which is as desired to reach a preferred target or region) coupled to a thermal energy source 914 (such as a Peltier junction or stack) and a temperature sensor 916 (in one embodiment, a temperature sensitive resistor). The thermal probe 910 is otherwise relatively thermally insulated. As shown the thermal energy source 914 and the temperature sensor 916 are electrically coupled to a switch 918 facilitating the use of a single set of control wires, and as with the optical probe 810, the switch 918 may be omitted in favor of multiple connections. The switch 918 need not be as complex and the buffer 820 (FIG. 8), as thermography calls for temperature measurements to be obtained after thermal stimulation is applied; simultaneous operation of the thermal energy source 914 and the temperature sensor 916 is generally not required. The switch is advantageously operated via signals from the device 110.

Thermographic measurement of perfusion is generally accomplished by applying a caloric stimulus (via the thermal energy source 914), either hot or cold, and measuring the temperature over an interval thereafter to determine how quickly heat dissipates. Increased dissipation correlates with higher blood flow. Thermographic techniques, and their calibration, are well known to practitioners of ordinary skill. As with optical measurements, thermographic measurements of perfusion are most useful in a relative sense, compared to a previously measured baseline, and may be subject to long term changes.

Thermal stimulation may also be performed by the probe 910 to modulate cerebral perfusion; generally, an increase in temperature will tend to increase blood flow in the region, and a decrease in temperature will lead to lower blood flow. Preferably, when measurements are to be made, smaller perturbances to temperature are preferred. Thermographic probes as generally described herein are commercially available.

Figure 10:
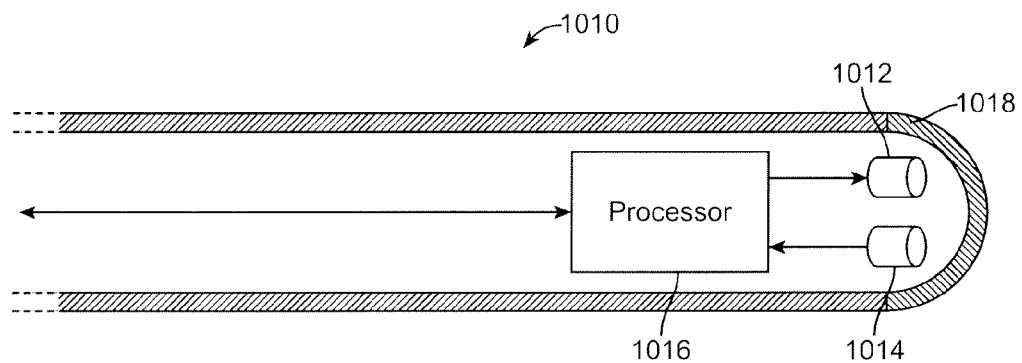
FIG. 10 is a schematic cutaway diagram of an ultrasonic sensing and stimulation probe according to the invention.

FIG. 10 illustrates a sonic probe 1010, which can include an ultrasonic transmitter 1012, an ultrasonic receiver 1014, and a processor 1016 all behind a partially acoustically transparent distal probe tip 1018. In the disclosed embodiment, the ultrasonic probe 1010 is adapted to measure perfusion via flowmetry (e.g., laser or ultrasound Doppler flowmetry), a technique well known in the art. The disclosed embodiment includes the Doppler processing in the probe via the processor 1016, though the calculations may also be performed on board the device 110.

The ultrasonic transmitter 1012 is, in the disclosed embodiment, a piezoelectric transducer configured to operate at a frequency greater than approximately 1 MHz. The ultrasonic receiver 1014 is adapted to receive at a range of similar and compatible frequencies. Pulsed measurements enable selection of measurement depth (e.g., the distance in front of the probe 1010 from which a measurement is taken), but in a presently preferred embodiment of the invention, measurements are taken in near proximity to the sensor.

Sonic stimulation may also be performed, for example using an ultrasonic probe 1010 according to the invention; ultrasonic stimulation generally operates to increase perfusion at the stimulation site. Different patterns of periodic, continuous, or responsive sonic stimulation may be used to cause different changes in perfusion, for example, stimulation of contralateral structures may decrease perfusion at an intended ipsilateral (to sensor) site.

Ultrasonic flow probes potentially suitable for use in connection with various embodiments of the present invention are commercially available. Regardless of the embodiment, when placing an ultrasonic probe, it is particularly important to avoid air bubbles and other gas pockets in front of the transducer, as such obstructions may confound measurements.

When used with the stimulator of FIG. 4, the probes described herein, such as those shown in FIGS. 6-13, can serve merely as stimulation devices without providing sensing.

Figure 11:
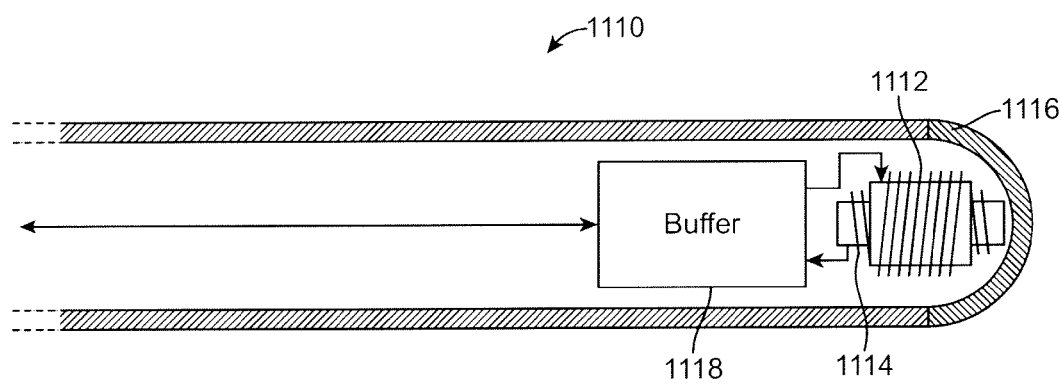
FIG. 11 is a schematic cutaway diagram of an electromagnetic sensing and stimulation probe according to the invention.

FIG. 11 illustrates an electromagnetic probe 1110 according to the invention, which includes a first field generating coil 1112 and a second sensing coil 1114 behind a magnetically permeable tip 1116. As with the other probe embodiments, a buffer 1118 is provided to enable a single set of control wires to be used and to offload some processing from the device 110.

The electromagnetic probe 1110 is capable of measuring blood flow volume and rate by applying a magnetic field with the first field generating coil 1112 and measuring changes in electrical potential created across the second sensing coil 1114 caused by the movement of ferromagnetic or polarized objects, in the present case blood cells, within the field. The general technique of flowmetry, such as electromagnetic flowmetry, is well known.

Localized electromagnetic stimulation may also be applied by the electromagnetic probe 1110. Depolarization potentially caused by a magnetic field may have therapeutic effects at or near a seizure focus or at a functionally relevant brain structure, or the magnetic field may be manipulated to affect perfusion in a desired manner according to the invention. In an embodiment, transcranial magnetic stimulation may be applied at a global scale (e.g., through the interface device 324, FIG. 3) to accomplish similar results.

Figure 12:
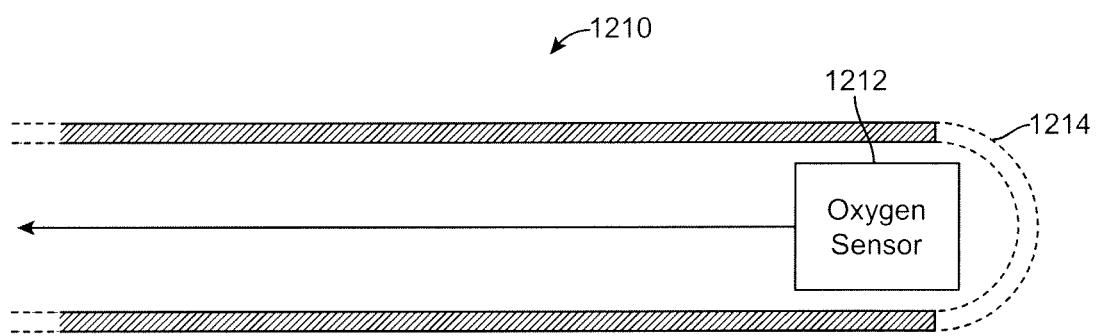
FIG. 12 is a schematic cutaway diagram of an electrochemical sensing probe according to the invention.

FIG. 12 illustrates an electrochemical oxygen probe 1210, which includes an oxygen sensor 1212 disposed behind a permeable tip 1214 or membrane. There are three common types of dissolved oxygen sensing probes: polarographic sensors, galvanic sensors, and optical fluorescence sensors, any of which may be adapted to serve the purposes of the invention to the extent they are biocompatible for long term implant purposes. Dissolved oxygen levels correlate positively with perfusion levels, and may be used by systems and methods according to the invention to measure blood flow and gas composition. The disclosed oxygen probe 1210 is not adapted to perform stimulation.

Other types of electrochemical sensing probes may also be used in this application, such as those detecting the presence of lactate in the neural tissue. These chemical markers may also be indicators of abnormal metabolism and perfusion levels.

Figure 13:
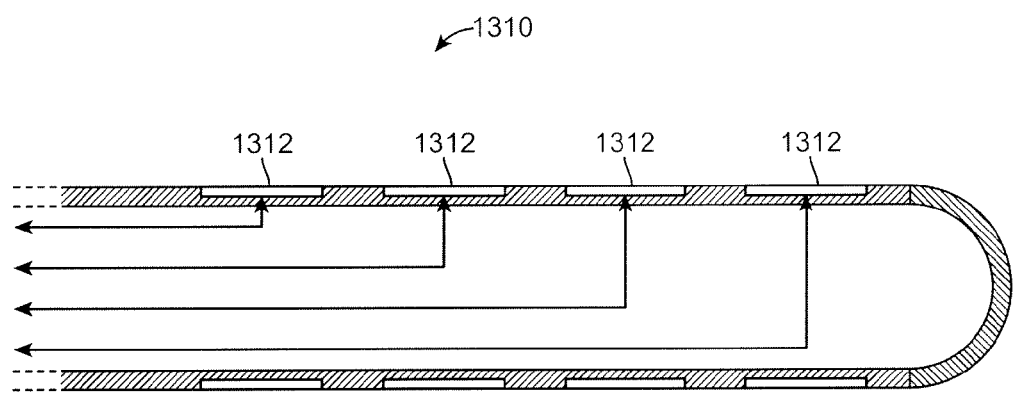
FIG. 13 is a schematic cutaway diagram of an electrical sensing and stimulation lead according to the invention.

A lead 1310 with four ring electrodes 1312 is illustrated in FIG. 13. In addition to traditional electrographic sensing and electrical stimulation as described above, the lead 1310 can be used to measure local perfusion by impedance imaging. Accordingly, low current and short pulses of electrical stimulation (to avoid undesired depolarization and electrographic interference artifacts, and to improve battery life) are applied and impedance is measured between a pair of electrodes 1312 on the lead 1310. Impedance imaging techniques such as plethysmography can be performed, where the image is constructed in two dimensions. These methods may also be termed impedance tomography or ECCT (electric current computed tomography).

As with other measurements described herein, electrical impedance plethysmography is advantageously used in a relative comparison to baseline measurements, rather than as an absolute value. Further, compensation for routine heart rhythm based variations (by taking average or peak values over several measurements) is also deemed advantageous.

With a sufficient number of electrodes disposed around a target site, it is possible to use a series of impedance measurements between different sets of electrodes to reconstruct a tomographic image of blood flow; techniques for accomplishing electrical impedance tomography are well known. In a presently preferred embodiment, data is collected for tomographic measurements by the device 110 and transferred to the programmer 312 or other external apparatus, where the intensive computations needed to reconstruct visualizations are more feasibly carried out.

Figure 14:
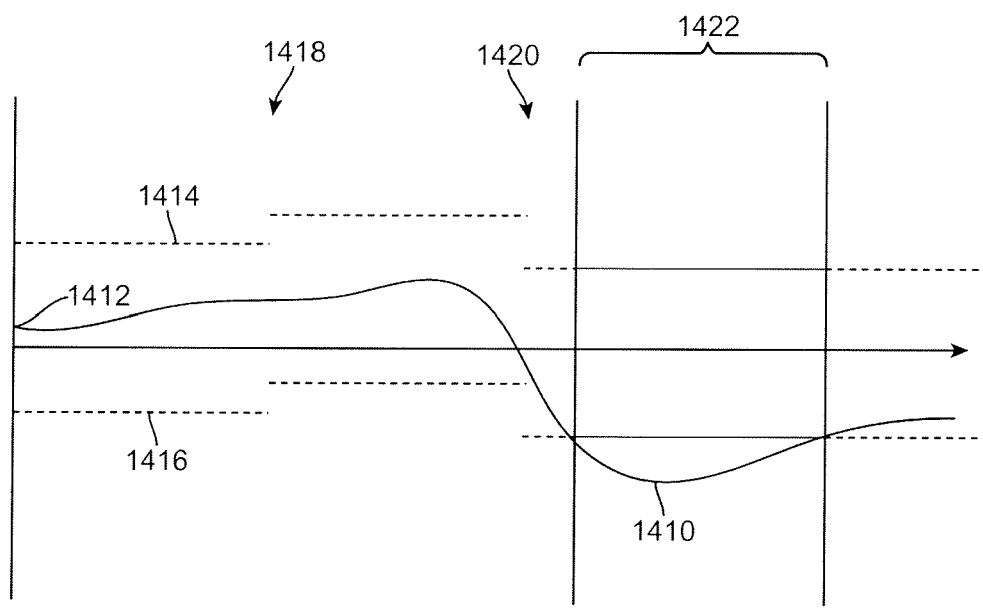
FIG. 14 is an exemplary graph of cerebral blood flow measurements in relation to thresholds calculated according to the invention.

FIG. 14 illustrates a sample hypothetical graph of cerebral perfusion measurements. At its start 1412, a perfusion curve 1410 (not illustrated to any particular scale) is approximately centered between an upper threshold 1414 and a lower threshold 1416. The perfusion curve 1410 shows gradually increasing perfusion up to a first time 1418, at which thresholds 1414 and 1416 are recalculated to accommodate long term trending. The thresholds 1414 and 1416 are recalculated again at a second time 1420, and shortly thereafter at a third time 1422 and the curve 1410 starts to drop below the lower threshold 1416. This drop below an adjusted threshold indicates, in an exemplary system or method, an undesired drop in perfusion, indicating that a therapeutic action should be taken as discussed in connection with the flow chart of FIG. 15 below. In an embodiment, cerebral blood flow is directly modulated (by means described herein) to increase it above the threshold 1416, or other actions may be taken alone or in conjunction with blood flow modulation.

During the time period 1422 the curve 1410 is below the lower threshold 1416, the thresholds 1414 and 1416 are not recalculated. Thresholds are readjusted periodically, e.g., step 1524 (in a preferred embodiment, a selectable number of seconds must pass before the readjustment occurs).

In one embodiment, the curve 1410 represents a condition which is calculated from the ratio of two or more measures, where one of the measures is representative of a characteristic of tissue that is relatively proximate to the location of a neurological event such as a seizure focus (i.e., an associated area), and where the other measures are representative of a characteristic of tissue that is relatively distal to the location of a neurological event (i.e., non-associated area), for example, outside of the focus of epileptiform activity. For example, the condition can be calculated as the ratio between perfusion in the region of a seizure focus and perfusion in a contralateral area. Alternatively, the condition can be calculated as the ratio between spectral power in a selected high frequency range in the region of a seizure focus and a measurement of this power at multiple probes which sense activity from regions located more distal to the focus. Further, the condition can be calculated with respect to norm data, such as self-norm data. For example, the curve 1410 can represent the current $HbO_2$ relative to the average ($HbO_2$+HbR) value for the last hour. NIRS data can be combined with, or measured in relation to, pulse oximetry, such as only measuring NIRS data at the peak of the EKG. Further, central NIRS data can be measured in the context of other measurement of arterial oxygen saturation, or other arterial gas estimations, measurements of trancutaneous oxygen and carbon dioxide, measures of systemic circulation as monitored by electrocardiograph and invasive or non-invasive blood monitors, in order to obtain a measurement of peripheral changes which can affect central NIRS readings. In other words, NIRS data and changes can be evaluated relative to peripheral changes in order to provide more accurate sensing and decrease false detections. The condition can be calculated based upon the change detected centrally, in the brain, with respect to a peripheral change. The condition representing a brain measurement can be calculated as a ratio including, for example, heart rate or blood pressure. The condition can also be assessed conditionally, for example, the curve 1410 is only assessed when peripheral measurements have certain values. For example, when a posture/position measurement indicates that a patient has transitioned from lying down to standing up, the baseline may be recomputed, and the curve 1410 is not reassessed until a specified duration, e.g., 20 seconds, has elapsed.

The condition in the signal being sensed 1410 can be additionally evaluated by evaluating temporal changes in a manner other than using thresholds (or guard bands) as shown in FIG. 14. For example, the rate of change of the signal, as reflected in the slope, can be evaluated, wherein when the slope is above a specified level, for a specified amount of time, then stimulation occurs. Other measures that may be used to evaluate the temporal patterns that characterize the condition of the signal being measured 1410 include those usable to analyze biological responses such as Galvanic skin response (e.g., time until, or value at, half-maximum which occurs after an event, total area under the curve over time). The condition of the signal being computed can be the z-transform of a measure of the signal, wherein, for example, any value over 2 or under −2 indicates that a statistically significant change has occurred.

Figure 16:
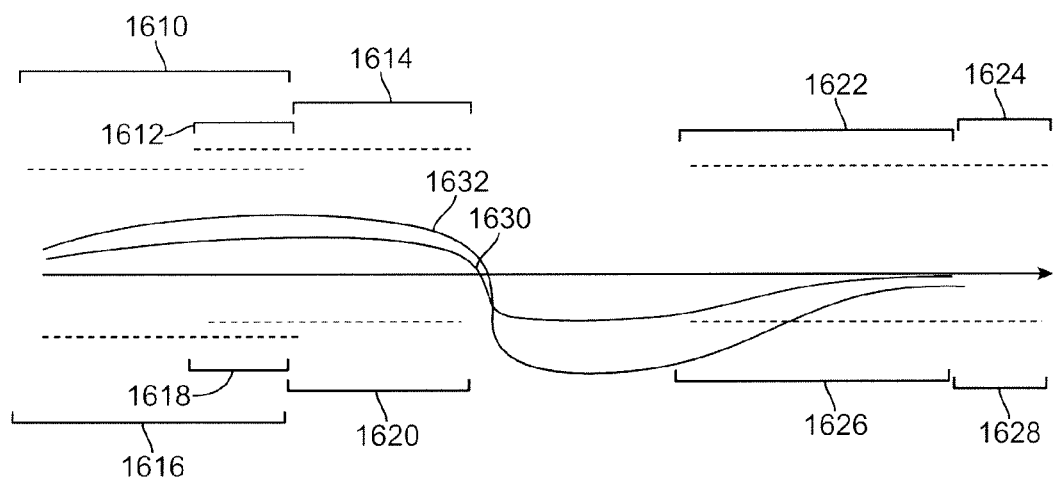
FIG. 16 is an exemplary graph of cerebral blood flow measurements in relation to dynamically altered threshold and guard bands calculated according to the invention.

In FIG. 14, the guard bands (thresholds) are recalculated at certain specified times. The guard bands can also be recalculated based upon the signal 1412 being evaluated. In other words, the duration of the window in which the guard bands are calculated can be adaptively defined based upon the characteristics of the sensed data. In one example, of the change in the signal 1410 is larger, then the duration of the window may be decreased according to a rule. For example, for every increase of X units in signal amplitude, the duration of the window is decreased by Y percent. The signal 1410 can also be used to change the post-event window used in subsequent analysis of activity. For example, as shown in FIG. 16, the duration of the guard bands can be based upon the signal. In FIG. 16, guard bands 1610 and 1616 occur first and then are followed by bands 1614 and 1620. When the exemplary signal 1630 is sensed, then the slope of the descent combined with the total descent of the curve is small enough that it causes the pre-drop guard bands to be recalculated on data in the sensed signal 1630 which spans across the durations 1612 and 1614, and the durations 1616 and 1620. When the sensed signal is like the signal 1632, then the change is significant enough that an event is detected without recalculation of the guard bands. In this manner, the amount of data used to calculate the guard bands can be adjusted based upon the measurement of the signal itself and therefore the detection of events occurs adaptively. Additionally, the length of the data which is examined in the post-event period can be based upon the characteristics of the event. For example, curve 1632 has a change that is large enough that the guard bands 1622 and 1626 are utilized. If a seizure-related change in perfusion is going to occur, it will do so temporally close to the event just detected. If curve 1630 occurs, then the calculation of guard bands may occur using a longer period. Additionally, the guard bands can be applied to other data being sensed. For example, if the data sensed is like the curve 1630, rather than like the curve 1632, then the post-event time for which a specific EEG criterion may be activated may be made longer or shorter. Alternatively, different EEG detection algorithms can be invoked based upon the characteristics of the signals 1630 and 1632.

Figure 15:
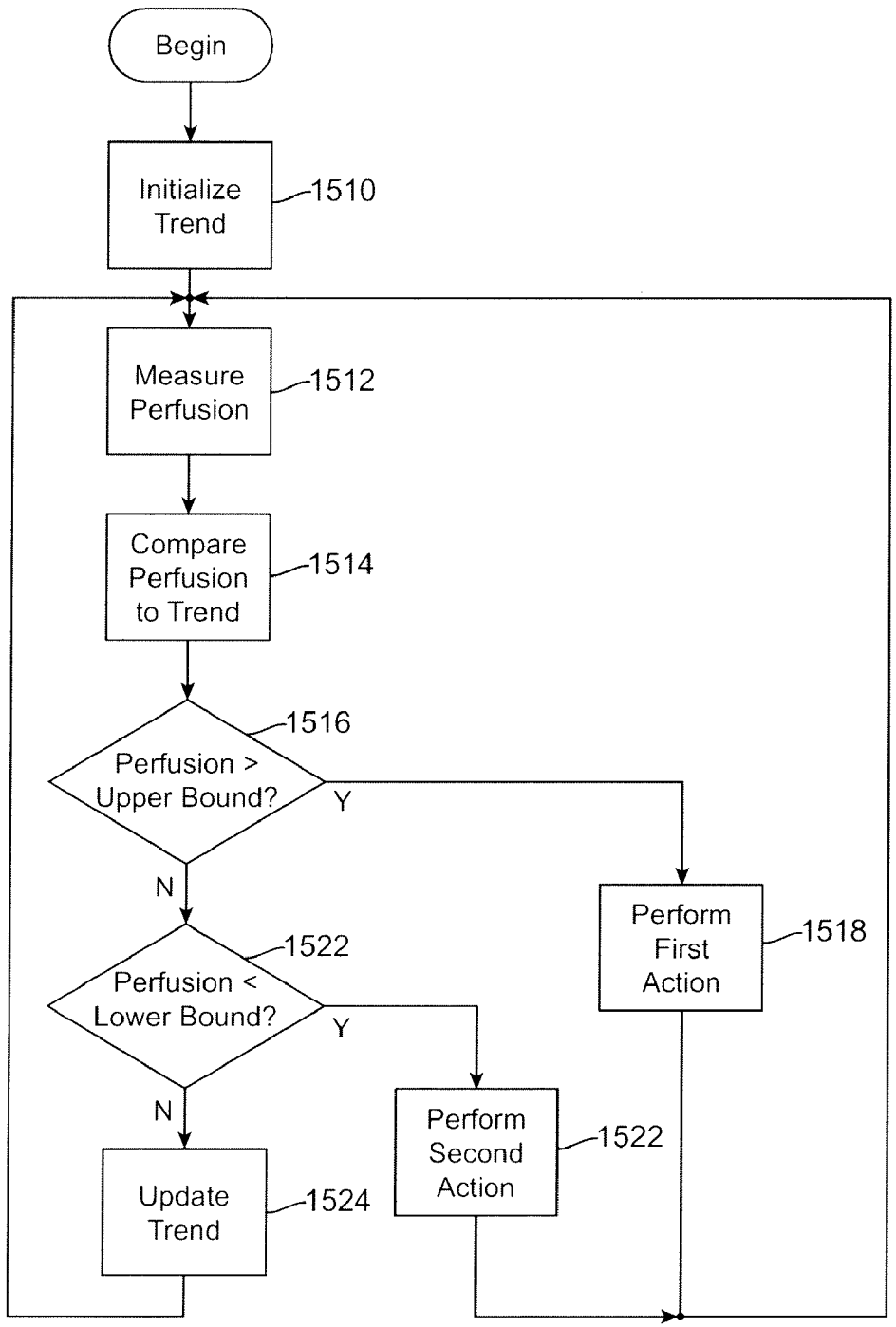
FIG. 15 is a flow chart illustrating an exemplary sequence of steps performed in measuring cerebral blood flow and responding to treat epilepsy and other disorders according to the invention.

A method according to the invention is performed, as illustrated in FIG. 15, by initializing a perfusion trend value (step 1510). This is performed by performing an initial perfusion measurement (or average of a sequence of measurements) and storing it in a trend variable.

Perfusion at a desired site is then measured (step 1512) by one of the methods described herein or any other applicable technique. The measurement is then compared (step 1514) to the previously calculated trend. If the perfusion measurement exceeds an upper bound (step 1516), namely the trend value plus an upper threshold value (or in an alternative embodiment, the trend value multiplied by an upper threshold factor generally greater than one), then a first action is performed (step 1518). This condition, when the perfusion exceeds a threshold, indicates hyperperfusion that may be an undesired or pathological condition, or at least an indication that conditions are out of equilibrium and require therapeutic intervention.

To treat hyperperfusion, stimulation may be applied to the patient's caudate nucleus; stimulating other anatomical targets may also serve to decrease perfusion. An audio alert, somatosensory stimulation, or other indication may also be provided to the patient or a caregiver via the implantable neurostimulator device 110 or its communication subsystem 530 (FIG. 5).

If the perfusion measurement exceeds (i.e., is lower than) a lower bound (step 1520), namely the trend value minus a lower threshold value (or in an alternative embodiment, the trend value multiplied by a lower threshold factor generally less than one), then a second action is performed (step 1522). This condition, when the perfusion is lower than a threshold, indicates hypoperfusion that may be an undesired or pathological condition suggestive of an imminent epileptic seizure. Hypoperfusion may be treated by applying stimulation at or near the site where the hypoperfusion was observed. In the case of epilepsy, frequently this will be a seizure focus. As with hyperperfusion, feedback may be provided to the patient or caregiver. Alternatively, external therapy (such as transcranial magnetic stimulation) may be applied, either automatically or manually (based on an indication).

As set forth above, for either hyperperfusion or hypoperfusion, stimulation of a variety of anatomical targets may be performed according to the invention to produce beneficial changes in cortical blood flow to treat neurological disorders. Specifically, but not by way of limitation, potential stimulation targets include the cortex of the brain (including specialized structures such as the hippocampus), white matter, basal ganglia (including the caudate nucleus), the brain stem, the spinal cord, the cerebellum or any of various cranial or peripheral nerves including the vagus nerve. Somatosensory stimulation (including sound, vision, and touch) may be suitable in some circumstances, particularly for acute therapy.

If the perfusion is within bounds, the trend variable is updated (step 1524) preferably periodically as described above. The method proceeds by repeating a perfusion measurement (step 1512) and continuing.

The actions taken need not be therapeutic in nature; they may serve other purposes. In one embodiment, the implantable device 110 is essentially a seizure counter adapted to identify and collect information about periods of abnormal perfusion for later retrieval.

The flow chart of FIG. 15 is not an exclusive description of methods performed by a system according to the invention. Rather, it describes a single aspect of a single embodiment of a system according to the invention for observing blood flow and taking action in response to changes. This method may be performed in conjunction with, or in parallel with, other methods generally performed by implantable devices and implantable neurostimulators specifically. In particular, cerebral blood flow management may be considered a useful adjunctive therapy for an implanted responsive neurostimulator such as that described in U.S. Pat. No. 6,810,285 to Pless et al., referenced above, that is also capable of applying pulsatile electrical stimulation in response to detected abnormal electrographic activity.

One possible clinical scenario is as follows. Consider a patient in which hypoperfusion is exhibited on the side of the brain where the patient's epileptiform activity originates. In the contralateral side, perfusion may be normal. This is considered to be a likely scenario, though by no means the only possible scenario. Some time before an epileptic seizure is likely to occur, perfusion starts to rise in the epileptic hemisphere, and plunges abruptly in the contralateral hemisphere just prior to the seizure. In this scenario, two parallel courses of the flow illustrated in FIG. 14 are contemplated, each one measuring perfusion in an area of interest in opposite hemispheres.

Interictally, while perfusion is low in the epileptic (hypoperfused) hemisphere, a system can be programmed to deliver electrical stimulation to increase perfusion and normalize the system. Each burst of stimulation tends to have a short term effect. Stimulation may be provided intermittently but regularly, while perfusion is monitored. If perfusion rises beyond the amount caused by the interictal stimulation, and especially if it is accompanied by a drop in perfusion in the contralateral hemisphere, then seizure activity may be anticipated. Accordingly, the stimulation strategy is altered in light of the changed brain state, and an alternative course of therapy is initiated, which may include some or all of the following: (1) stimulation of the caudate nucleus to decrease excitability in the epileptic hemisphere; (2) stimulation of the cortical or sub-cortical structures of the contralateral hemisphere to increase perfusion there; and (3) therapeutic electrical stimulation to reduce the likelihood of seizure activity. If ictal electrographic activity is then also observed in a system, further actions may also be taken. Different actions may also be taken depending on whether the patient is asleep or awake (as potentially indicated by electrographic activity) or based on other measures of level of arousal or activity, as these factors may also tend to affect perfusion.

It should be observed that while the foregoing detailed description of various embodiments of the present invention is set forth in some detail, the invention is not limited to those details and an implantable medical device or system made according to the invention can differ from the disclosed embodiments in numerous ways. In particular, it will be appreciated that embodiments of the present invention may be employed in many different applications to responsively treat epilepsy and other neurological disorders. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. A method for responding to a neurological disorder in a human patient comprising:
    obtaining a perfusion measurement with an implantable device;
    identifying a change in the cerebral perfusion measurement;
    in response to the change, performing an action; and
    identifying a structure in a hemisphere demonstrating increased blood flow, and wherein performing the action comprises stimulating a neural structure in a hemisphere contralateral to the hemisphere demonstrating a structure with the increased blood flow.

2. A method for responding to a neurological disorder in a human patient comprising:
    obtaining a perfusion measurement with an implantable device;
    identifying a change in the cerebral perfusion measurement; and
    in response to the change, performing an action, wherein obtaining the cerebral perfusion measurement comprises:
        observing a first signal from a first implanted sensor;
        observing a second signal from a second implanted sensor; and
        calculating the perfusion as a composite of the first signal and the second signal, wherein the first implanted sensor is positioned to measure the first signal from an artery feeding a location and the second implanted sensor is positioned to measure the second signal from a vein leaving the location.

3. A method for responding to a neurological disorder in a human patient comprising:
    obtaining a perfusion measurement with an implantable device;
    identifying a change in the cerebral perfusion measurement; and
    in response to the change, performing an action, wherein obtaining the cerebral perfusion measurement comprises:
        observing a first signal from a first implanted sensor;
        observing a second signal from a second implanted sensor; and
        calculating the perfusion as a composite of the first signal and the second signal, wherein performing the action comprises:
            delivering a therapy to modulate the cerebral perfusion measurement, wherein delivering the therapy causes the first signal to more closely resemble the second signal.

* * * * *